US010074805B2

(12) United States Patent
Tanabe et al.

(10) Patent No.: US 10,074,805 B2
(45) Date of Patent: Sep. 11, 2018

(54) FLUORESCENT ORGANIC LIGHT EMITTING ELEMENTS HAVING HIGH EFFICIENCY

(71) Applicant: UDC IRELAND LIMITED, Dublin (IE)

(72) Inventors: Junichi Tanabe, Dublin (IE); Flavio Luiz Benedito, Dublin (IE); Christian Lennartz, Dublin (IE)

(73) Assignee: UDC Ireland Limited, Dublin (IE)

( * ) Notice: Subject to any disclaimer, the term of this patent is extended or adjusted under 35 U.S.C. 154(b) by 0 days.

(21) Appl. No.: 15/500,853

(22) PCT Filed: Sep. 16, 2015

(86) PCT No.: PCT/EP2015/071164
§ 371 (c)(1),
(2) Date: Jan. 31, 2017

(87) PCT Pub. No.: WO2016/046034
PCT Pub. Date: Mar. 31, 2016

(65) Prior Publication Data
US 2017/0263868 A1 Sep. 14, 2017

(30) Foreign Application Priority Data

Sep. 22, 2014 (EP) .................................. 14185760

(51) Int. Cl.
*C07D 401/04* (2006.01)
*C07D 471/06* (2006.01)
*H01L 51/00* (2006.01)
*C09K 11/02* (2006.01)
*C09K 11/06* (2006.01)
*H01L 51/50* (2006.01)

(52) U.S. Cl.
CPC ........ *H01L 51/0053* (2013.01); *C07D 401/04* (2013.01); *C07D 471/06* (2013.01); *C09K 11/025* (2013.01); *C09K 11/06* (2013.01); *H01L 51/0072* (2013.01); *C09K 2211/1007* (2013.01); *C09K 2211/1022* (2013.01); *C09K 2211/1044* (2013.01); *C09K 2211/1059* (2013.01); *H01L 51/5016* (2013.01)

(58) Field of Classification Search
CPC .. H01L 51/0053; C07D 401/04; C07D 471/06
USPC ........................................................ 252/500
See application file for complete search history.

(56) References Cited

U.S. PATENT DOCUMENTS

2007/0073503 A1   3/2007   Kimura et al.

FOREIGN PATENT DOCUMENTS

| JP | 2008103475 | 5/2008 |
| WO | 2007120788 | 10/2007 |
| WO | 2012001002 | 1/2012 |

OTHER PUBLICATIONS

Mei el al. Polymer (2006), 47(14), 4976-4984.*
Kim et al., 2012, Thermally Stable Carbazole-Diimides as Hole Transport Materials for Organic Light-Emitting Devices, J. Nanoscience and Nanotechnology, 12:4219-4223.
Skorodumov et al., 1967, "Synthesis in the phenothiazine series XIX. 3-Aminophenothiazine," Chemistry of Heterocyclic Compounds 3:62-63.
Wang et al., "An efficient guest/host fluorescent energy transfer pair based on the napthalimide skeleton, and its application in heavily-doped red organic light-emitting diodes," Dyes and Pigments 100:87-96.
Feng et al., 2008, "Synthesis and optical properties of novel compounds containing carbazole and 1,8-naphthalimide groups," J. Chem. Res. 3:137-140.
Gudeika et al., 2015, "Structure-properties relationship of the derivatives of carbazole and 1,8-naphthalimide: Effects of the substitution and the linking topology," Dyes and Pigments 114:239-252.
Martinez-Viturro et al., 2007, "Synthesis of aza analogues of the anticancer agent batracylin," Tet. Lett. 48:4707-4710.
Koyuncu et al., "A novel donor-acceptor polymeric electrochromic material containing carbvazole and 1,8-naphthalimide as subunit," Eiectrochimica Acta 55:4935-4971.
Lee et al., "Green polymer-light-emitting-diodes based on polyfluorenes containing N-aryl-1,8-naphthalimide and 1,9-naphthoilene-arylimidazole derivatives as color tuner," Polymer 50:5668-5674.
Zhou et al., "Charge-transfer-featured materials-promising hosts for fabrication of efficient OLEDs through triplet harvesting via triplet fusion," Chem. Comm. 50:7586.
Endo, 2009, "Thermally Activated Delayed Fluorescence from Sn4þ-Porphyrin Complexes and Their Application to Organic Light-Emitting Diodes—A Novel Mechanism," for Electroluminescence Adv. Mater. 21:4802.
Endo, 2011, "Efficient up-conversion of triplet excitons into a singlet state and its application for organic light emitting diodes," App. Phys. Lett. 98:083302.
Nakagawa, 2012, "Electroluminescence based on thermally activated delayed fluorescence generated by a spirobifluorene donor-acceptor structure," Chem. Comm. 48:9580.
Al-Asbahi et al., 2013, "Photophysical properties and energy transfer mechanism of PFO/Fluorol 7GA hybrid thin films," J. Luminescence 142:57-65.
Jin and Tang, 2013, "Theoretical study on optical and electronic properties of bipolar molecules with 1,8-naphthalimide and triphenylamine moieties as organic light-emitting materials," J. Mol. Graphics Modelling 42:120-128.

(Continued)

Primary Examiner — Kahsay Habte
(74) Attorney, Agent, or Firm — Riverside Law LLP

(57) ABSTRACT

The present invention relates to organic light emitting elements, comprising thermally activated delayed fluorescence (TADF) emitters and/or hosts on basis of phthalimide and naphthalimide materials, which have a sufficiently small energy gap between $S_1$ and $T_1$ ($\Delta E_{ST}$) to enable up-conversion of the triplet exciton from $T_1$ to $S_1$. The organic light emitting elements show high electroluminescent efficiency.

21 Claims, No Drawings

(56) References Cited

OTHER PUBLICATIONS

Wang et al., 2012, "Synthesis, spectroscopic characteristic of novel fluorescent dyes of pyrazoline compounds," Spectrochimica Acta Part A 93:343-347.

Dobrikov et al., 2011, "Synthesis and electronic spectra of new low-molecular weight compounds with possible application in electroluminescent layers," Cent. Eur. J. Chem. 9:1126-1132.

Liu et al., 2006, "Highly efficient green light emitting polyfluorene incorporated with 4-diphenylamino-1,8-naphthalimide as green dopant," J. Mater. Chem. 16:1431-1438.

Liu et al., 2006, "Blue light-emitting polymer with polyfluorene as the host and highly fluorescent 4-dimethylamino-1,8-naphthalimide as the dopant in the sidechain," Appl. Phys. Lett. 88:083505.

Wang et al., 2005, "Luminescent properties of a novel naphthalimide-fluorene molecule," Synthetic Metals 150:33-38.

Gan et al., 2004, "1,8-Naphthalimides for non-doping OLEDs: the tunable emission color from blue, green to red," J, Photochemistry Photobiology A: Chem. 162:399-406.

Jiang et al., 1997, An electrolurninescent device made with a new fluorescent dye containing 1,3,4-oxadiazole J. Mater. Chem. 7:1395-1398.

Jin et al., 2014, "Rational design of donor-π-acceptor n-butyl-1,8-naphthalimide-cored branched molecules as charge transport, and luminescent materials for organic light-emitting diodes," Tetrahedron 70:47-53.

Ulla et al., 2014, "Blue organic light emitting materials: Synthesis and characterization of novel 1,8-naphthalimide derivatives," Optical Materials 36:704-711.

Wang et al., 2010, "The synthesis and photoluminescence characteristics of novel blue light-emitting naphthalimide derivatives," Dyes and Pigments 86:190-196.

Marom et al., 2011, "Toward the Development of the Direct and Selective Detection of Nitrates by a Bioinspired Mo—Cu System," Org. Lett. 13:5532-5535.

\* cited by examiner

FLUORESCENT ORGANIC LIGHT EMITTING ELEMENTS HAVING HIGH EFFICIENCY

CROSS-REFERENCE TO RELATED APPLICATIONS

This application is the U.S. National Stage Application filed under 35 U.S.C. § 371 claiming benefit to International Patent Application No. PCT/EP2015/071164, filed Sep. 16, 2015, which is entitled to priority under 35 U.S.C. § 119 (a)-(d) to EP Application No. 14185760.7, filed Sep. 22, 2014, each of which is hereby incorporated by reference in its entirety.

The present invention relates to organic light emitting elements, comprising thermally activated delayed fluorescence (TADF) emitters and/or hosts on basis of phthalimide and naphthalimide, which have a sufficiently small energy gap between $S_1$ and $T_1$ ($\Delta E_{ST}$) to enable up-conversion of the triplet exciton from $T_1$ to $S_1$. The organic light emitting elements show high electroluminescent efficiency.

The specifically substituted phthalimide and naphthalimide derivatives exhibit TADF (thermally activated delayed fluorescence) characteristics.

TADF is an effective triplet-harvesting process that involves up-conversion of triplet ($T_1$) to singlet ($S_1$) excited states. Derivatives exhibiting TADF characteristics are characterized by having a sufficiently small energy gap between $S_1$ and $T_1$ ($\Delta E_{ST}$) to enable up-conversion of the triplet exciton from $T_1$ to $S_1$.

The development of OLED luminescent materials is an important issue and these materials have been classified into two major categories. The first is fluorescent materials, which can harvest only the singlet excitons (25%) that are generated by electrical excitation. The second is phosphorescent materials, which can harvest the triplet excitons generated (75%). The branching ratio of singlet and triplet excitons is 1:3. Therefore, in recent devices, phosphorescent materials and their related technologies have been indispensable to obtain high EL efficiency. However, phosphorescent materials generally contain a rare metal element such as Ir or Pt. These metals are rather expensive and are dependent on limited global resources.

Recently, the alternative concept of thermally activated delayed fluorescence (TADF) as a third generation luminescent material, instead of the conventional fluorescent and phosphorescent materials was decribed by C. Adachi et al. in Adv. Mater., 2009, 21, 4802; Appl. Phys. Lett., 2011, 98, 083302 and Chem. Commun., 2012, 48, 9580.

The TADF strongly depends on HOMO-LUMO separation in a single molecule. TADF materials have a sufficiently small energy gap between $S_1$ and $T_1$ ($\Delta E_{ST}$) to enable up-conversion of the triplet exciton from $T_1$ to $S_1$. This small $\Delta E_{ST}$ enables TADF materials to realize 100% of the exciton formation generated by electrical excitation at $S_1$.

WO2007120788A1 relates to organic electronic devices comprising a phthalimide compound

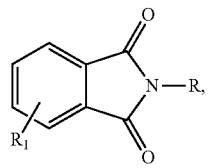

wherein $R_1$ represents one or more independently selected substitutions located on any position of the ring, wherein each substitution is a hydrogen, an alkyl moiety containing up to fifteen carbon atoms, or an aryl moiety, and wherein R is a phenyl group or a phthalimide-containing group. The phthalimide compounds disclosed in WO2007120788A1 are electron transporters with large HOMO-LUMO gaps, high triplet energies, large reduction potentials, and/or thermal and chemical stability.

Bandar Ali Al-Asbahi et al., Journal of Luminescence 142 (2013) 57-65, investigated the photophysicalproperties of poly(9,9'-di-n-octylfluorenyl-2.7-diyl)(PFO)/2-butyl-6-(butylamino)benzo[de]isoquinoline-1,3-dione (Fluorol7GA;

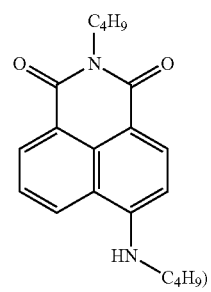

and the energy transfer between them.

Ruifa Jin, Shanshan Tang, Journal of Molecular Graphics and Modelling 42 (2013) 120-128, report on theorethical studies of a series of D-π-A bipolar molecules with triphenylamine (TPA) fragments as donors, 1,8-naphthalimide (NI) fragments as acceptors, and different π-conjugated bridges (CB) as π-conjugated bridges and their optical, electronic, and charge transport properties as charge transport and luminescent materials for organic light-emitting diodes (OLEDs).

Ruifa Jin, Shanshan Tang, J. Mol. Model. 19 (2013) 1685-1693 report on theorethical studies of a series of of 1,8-naphthalimide derivatives their optical, electronic, and charge transport properties as charge transport and/or luminescent materials OLEDs.

H.-Y. Wang et al., Spectrochimica Acta Part A 93 (2012) 343-347 reports the synthesis of four pyrazoline fluorescence dyes,

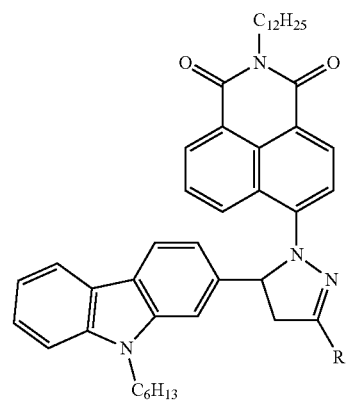

(R=Ph, Ph-OMe, Ph-NO$_2$, thiophene), and their characterization by means of $^1$H, $^{13}$C NMR, and HRMS.

WO2012001002A2 relates to a composition comprising an organic emitter molecule, this molecule having a ΔE(S$_1$-

$T_1$) value between the lowermost excited singlet state ($S_1$) and the triplet state beneath it ($T_1$) of less than 2500 cm$^{-1}$, and an optically inert atom or molecule for reducing the inter-system crossing time constant of the organic molecule to less than 10$^{-6}$ s.

Georgi H. Dobrikov et al., Cent. Eur. J. Chem. 9(6) (2011) 1126-1132 report the synthesis of two low-molecular weight compounds —(Z)-4-(4-(dimethylamino)benzylidene)-1-(9-ethyl-9H-carbazol-3-yl)-2-phenyl-1Himidazol-5(4H)-one and 2-(6-hydroxyhexyl)-6-(pyrrolidin-1-yl)-1H-benzo[de]isoquinoline-1,3(2H)-dione),

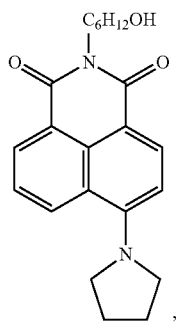

with possible application in organic light-emitting devices.

Jun Liu et al., J. Mater. Chem., 2006, 16, 1431-1438, report that highly efficient green light emitting polymers were obtained by covalently attaching just 0.3-1.0 mol % of a green dopant, 4-(N,N-diphenyl) amino-1,8-naphthalimide (DPAN), to the pendant chain of polyfluorene (the host).

Jun Liu et al., Applied Physics Letters 88 (2006) 083505, report that by covalently attaching 0.2 mol % highly fluorescent 4-dimethylamino-1,8-naphthalimide (DMAN) unit (photoluminescence quantum efficiency: φPL=0.84) to the pendant chain of polyfluorene, an efficient and colorfast blue light-emitting polymer with a dopant/host system can be obtained.

S. Wang et al., Synthetic Metals 150 (2005) 33-38, report on the synthesis of a naphthalimide-fluorene molecule, 4-(N,N-dimethylamino)-N-(2'-fluorenyl)-1,8-naphthalimide (DFN) and studies on its luminescent properties.

Jia-An Gan et al., Journal of Photochemistry and Photobiology A: Chemistry 162 (2004) 399-406, report that substitution at the 4-position of 1,8-naphthalimide with electron-donating groups can increase fluorescent quantum yields and change emissive wavelengths from blue to red.

Xuezhong Jiang et al., J. Mater. Chem. 7(8) (1997) 1395-1398, report an investigation on the use of a new derivative of 1,8-naphthalimide containing 1,3,4-oxadiazole for the fabrication of organic light emitting diodes.

Yi Wang et al., Dyes and Pigments 100 (2014) 87-96 discloses the synthesis of 11-tert-butyl-((E)-4-(2-(7-(diphenylamino)-9,9-diethyl-9Hfluoren-2-yl)vinyl)-7H-benzimidazo[2,1-a]benzo[de]isoquinolin-7-one and 2-(4-tert-butylphenyl)-6-(9-(4-tert-butylphenyl)-9H-carbazol-3-yl)-1H-benzo[de]isoquinoline-1,3(2H)-dione and their use as guest and host, respectively in OLEDs.

Rui-fa Jin et al., Tetrahedron 70 (2014) 47-53, reports the design of four D-π-A bipolar molecules with n-butyl-1,8-naphthalimide (BNI) fragments,

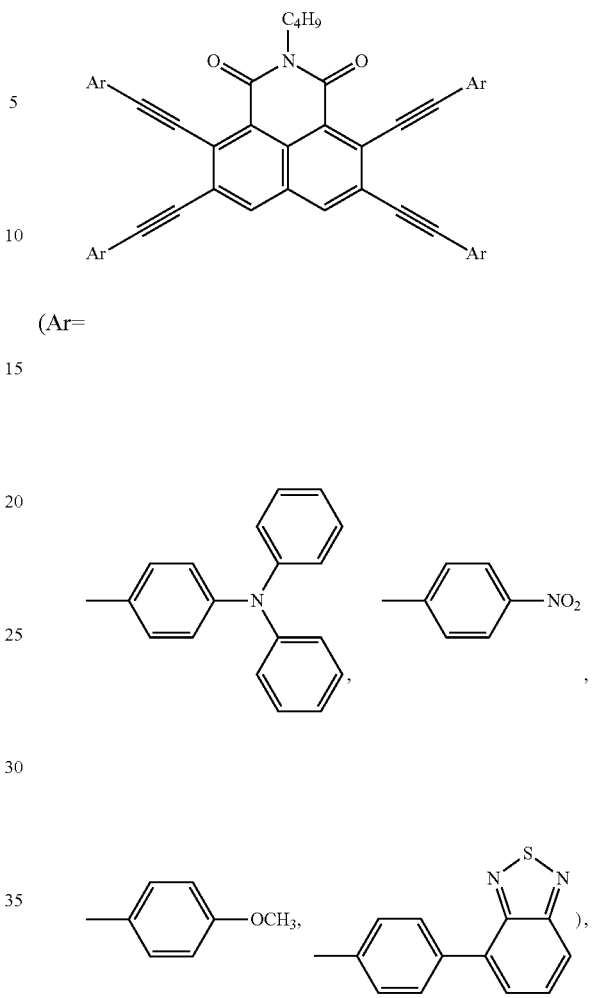

as acceptors, acetylenes as π-spacers, and different aromatic groups as donors to explore their optical, electronic, and charge transport properties as charge transport and luminescent materials for organic light-emitting diodes (OLEDs) by quantum-chemical studies.

H. Ulla et al., Optical Materials 36 (2014) 704-711 discloses the synthesis of series of naphthalimide derivatives which are substituted by electron-donating phenoxy groups at the 4$^{th}$ position of 1,8-naphthalimide. The photophysical studies revealed that by varying the substituents at the 4th position of the 1,8-naphthalimide backbone, the photoluminescence spectra can be readily tuned in the range 410-423 nm (solution) and 457-468 nm (thin film).

Yi Wang et al., Dyes and Pigments 86 (2010) 190-196 discloses that by substitution at the 4-position of 1,8-naphthalimide with electron-donating phenoxy or tert-butyl modified phenoxy groups, novel naphthalimide derivatives are obtained which emitts blue fluorescence with emission peaks of 425 and 444 nm in chloroform solution under UV irradiation, with highest relative photoluminescence quantum efficiency of 0.82.

Kim Chi-Wan et al., Journal of Nanoscience and Nanotechnology 12 (2012) 4219-4223 discloses carbazole-diimide derivatives of formulae BPCZ and 6FCZ as hole transport materials for OLEDs:

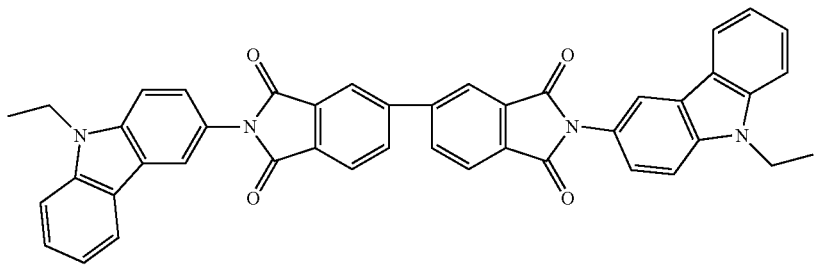

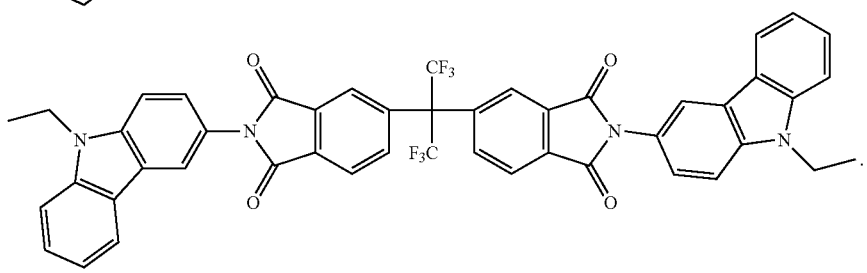

V. A. Skorodumov et al., Khimiya Geterotsiklicheskikh Soedinenii, Chemistry of Heterocyclic Compounds 3 (1967) 62-63 discloses thiazine-phthalimide derivatives of formulae IV and VIII:

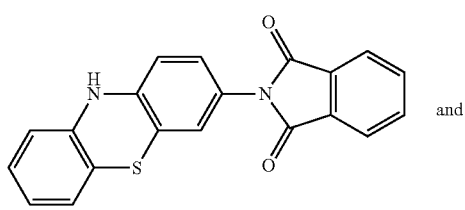

Wang Yi et al., Dyes and Pigments 100 (2007) 87-96 disclose naphthalimide derivatives as an efficient guest/host fluorescent energy transfer pair and its application properties in heavily-doped red organic light-emitting diodes.

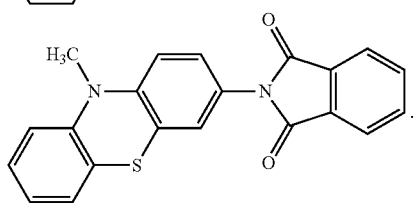

Journal of Chemical Research 3 (2008) 137-140 disclose naphthalimide derivatives as an efficient guest/host fluorescent energy transfer pair and its application properties in heavily-doped red organic light-emitting diodes.

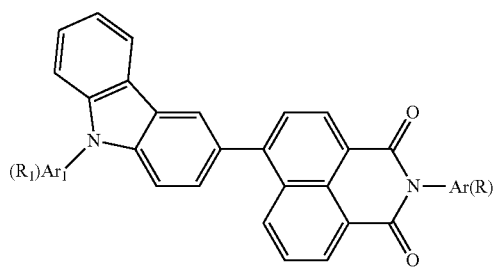

(3(a-h))

D. Gudeika et al., Dyes and Pigments 114 (2015) 239-252 (available online: Nov. 21, 2014) report the synthesis of a series of 1,8-naphthalimide and carbazole derivatives. These compounds exhibit high thermal stability with 5% weight loss temperature up to 476° C. Most of the synthesized compounds are capable of glass formation with glass transition temperatures from 30 to 87° C. Naphthalimide and carbazole donor-acceptor systems show broad unstructured fluorescence spectra peaking at 460-580 nm. Singly bonded 3-C-monosubstituted and 3,6-C-disubstituted compounds show pronounced positive solvatochromic effects with the reduction of the non-radiative recombination rate in polar solvents which results in high photoluminescence quantum yields up to 0.83.

An object of the present invention is to provide a highly efficient and practically useful organic light-emitting element and an organic light-emitting material suitable for the organic light-emitting element. It has surprisingly been found that certain phthalimide and naphthalimide compounds emit delayed fluorescence and the use thereof in an organic light-emitting element provides a highly efficient organic EL element.

Accordingly, the present invention relates to compounds of formula

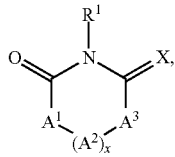
(I)

wherein

X is O, or $NR^2$;

$R^1$ is a $C_1$-$C_{25}$alkyl group, a $C_6$-$C_{10}$aryl group which is optionally substituted by one or more groups $R^8$;

$R^2$ is a $C_1$-$C_6$alkyl group, a $C_2$-$C_4$alkenyl group, or a $C_6$-$C_{10}$aryl group, which is optionally substituted by one or more groups $R^8$; or $R^1$ and $R^2$ together form a ring

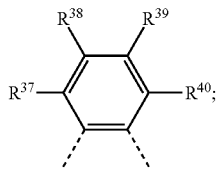

wherein $R^{37}$, $R^{38}$, $R^{39}$ and $R^{40}$ are independently of each other H, D, F, Cl, a $C_1$-$C_{25}$alkyl group, a $C_1$-$C_{25}$alkoxy group, a $C_6$-$C_{10}$aryl group which may optionally be substituted by one or more groups $R^8$, $A^1$, $A^2$ and $A^3$ are C, x is 0, or 1, if x is 0, $A^1$ and $A^3$ are connected via a double bond and together form a ring

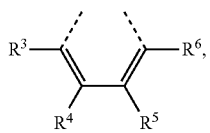

if x is 1, $A^1$ and $A^2$ and $A^2$ and $A^3$ are connected via a single bond and together form a ring system

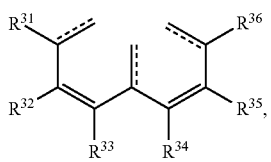

$R^3$, $R^4$, $R^5$, $R^6$, $R^{31}$, $R^{32}$, $R^{33}$, $R^{34}$, $R^{35}$ and $R^{36}$ are independently of each other H, D, F, Cl, a $C_1$-$C_{25}$alkyl group, a $C_1$-$C_{25}$alkoxy group, a $C_6$-$C_{10}$aryl group which may optionally be substituted by one or more groups $R^8$, or a donor group of formula

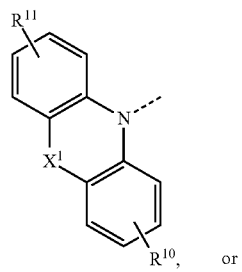
(Xa)

or

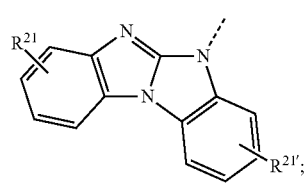
(Xd)

$R^8$ is D, F, Cl, a $C_1$-$C_{12}$alkyl group, a $C_1$-$C_{12}$alkoxy group, or a $C_6$-$C_{10}$aryl group;

$X^1$ is a direct bond, O, S, $N(R^{15})$, $C(=O)$, $C(R^{16})(R^{17})$, $B(R^{18})$, or $Si(R^{19})(R^{20})$, $R^{10}$, $R^{11}$, $R^{21}$ and $R^{21'}$ are independently of each other H, D, F, Cl, Br, or a $C_1$-$C_{25}$alkyl group;

$R^{15}$, $R^{16}$, $R^{17}$, $R^{18}$, $R^{19}$ and $R^{29}$ are independently of each other H, D, a $C_1$-$C_{25}$alkyl group, or a $C_6$-$C_{14}$aryl group, which can optionally be substituted by one, or more groups selected from a $C_1$-$C_{25}$alkyl group, a $C_1$-$C_{25}$alkoxy group and a $C_6$-$C_{10}$aryloxy group;

with the proviso that at least one of the groups $R^3$, $R^4$, $R^5$, $R^6$, $R^{31}$, $R^{32}$, $R^{33}$, $R^{34}$, $R^{35}$ and $R^{36}$ is a donor group of formula (Xa), or (Xd).

The present invention is also directed to the use of compounds of formula (I) for generating delayed fluorescence emission.

Thermally activated delayed fluorescence (TADF, E-type delayed fluorescence) is a promising way to obtain a high efficiency of exciton formation by converting spin-forbidden triplet excitons up to the singlet level by the mechanism of reverse intersystem crossing (RISC). In a TADF emitter, the upconversion mechanism uses the vibronic energy that, at sufficiently high temperatures 300 K), allows all of the excitons in an OLED to eventually produce light through singlet decay.

E-type delayed fluorescence fluorescence is defined herein as a process in which the first excited singlet state ($S_1$) becomes populated by a thermally activated radiationless transition from the first excited triplet state ($T_1$).

The present invention is also directed to an organic light-emitting element, comprising a compound of formula (I).

The organic light-emitting element offers an external quantum efficiency of more than 5%, especially more than 10% and reduced efficiency roll-off characteristics at high luminance.

The compound of formula (I) has preferably a difference between excited singlet energy and excited triplet energy (($\Delta E_{ST}$) of 0.5 eV or less, more preferably $\Delta E_{ST}$ of 0.35 eV or less, i.e. of 0.01 to 0.5 eV, especially 0.01 to 0.35 eV.

The determination of $\Delta E_{ST}$ can be carried either by quantum mechanical calculations (for example TD-DFT (time dependent density functional theory) calculations, for example with commercially available Gaussian 09 or ADF Amsterdam Density Functional software programs; for example as described in Adv. Mater. 2008, 20, 3325-3330), or experimentally.

Experimental Determination of $\Delta E_{ST}$:

i) $\Delta E_{ST}$ can be determined based on the information given in the following formula:

$$Int(S_1 \rightarrow S_0)/Int(T_1 \rightarrow T_0)=k(S_1)/k(T_1)\exp(-\Delta E/k_B T).$$

The intensites $Int(S_1 \rightarrow S_0)$ and $Int(T_1 \rightarrow T_0)$ can be determined spectroscopically by a spectrophotometer. A graph of the logarithmic intensity ratios $Int(S_1 \rightarrow S_0)/Int(T_1 \rightarrow T_0)$ measured at different temperatures versus the reciprocal of the absolute temperature T generally shows a straight line. The measurement is carried out in a temperature range from room temperature (300 K) to 77 K to 4.2 K (the temperature can be adjusted by means of a cryostat). The respective transitions $(S_1 \rightarrow S_0)$ and $(T_1 \rightarrow T_0)$ (band intensities) can be identified since the triplet transition is at lower energy than the singlet transition and increases in intensity with decreasing temperature. The measurements are usually performed in oxygen-free dilute solutions (about $10^{-2}$ mol$L^{-1}$) or thin films of the respective compounds or doped films comprising the corresponding compounds.

The slope of the straight line mentioned above is $-\Delta E/k_B T$. With $k_B=1.380\ 10^{-23}$ JK$^{-1}$=0.695 cm$^{-1}$ K$^{-1}$, $\Delta E_{ST}$ can be determined.

ii) $\Delta E_{ST}$ can also be determined by measuring the temperature dependency of the emission decay as known by a person skilled in the art.

iii) An approximate estimation of $\Delta E_{ST}$ can be achieved by recording the fluorescence and phosphorescence spectra at low temperature (for example 77 K or 4.2 K using a cryostat). $\Delta E_{ST}$ then corresponds to an approximation of the energy difference between the high-energy rising edges of the fluorescence or phosphorescence band.

The compounds of formula (I) contain preferably one, or two donor groups of formula (Xa) and/or (Xd).

Among the compounds of formula (I) compounds of formula

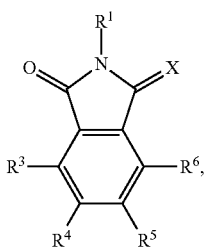

(II)

wherein X, R$^1$, R$^3$, R$^4$, R$^5$ and R$^6$ are as defined above, and compounds of formula

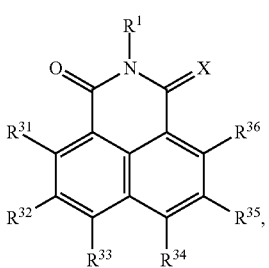

(III)

wherein X, R$^1$, R$^{31}$, R$^{32}$, R$^{33}$, R$^{34}$, R$^{35}$ and R$^{36}$ are as defined above, are preferred.

Among the compounds of formula (II) compounds of formula

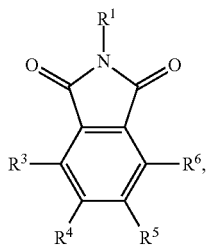

(IIa)

wherein R$^1$, R$^3$, R$^4$, R$^5$ and R$^6$ are as defined above, and compounds of formula

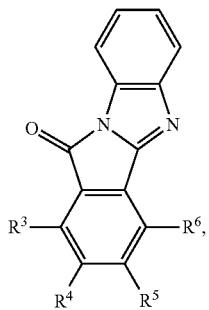

(IIb)

wherein R$^3$, R$^4$, R$^5$ and R$^6$ are as defined above, are more preferred.

Compounds of formula

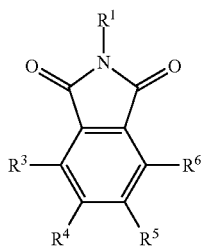

(IIa)

are even more preferred, wherein

R$^3$, R$^4$, R$^5$ and R$^6$ are independently of each other a donor group of formula (Xa), or (Xd); or R$^3$ and R$^6$ are H and R$^4$ and R$^5$ are independently of each other a donor group of formula (Xa), or (Xd); or R$^4$ and R$^5$ are H and R$^3$ and R$^6$ are independently of each other a donor group of formula (Xa), or (Xd); or R$^4$ and R$^6$ are H and R$^3$ and R$^5$ are independently of each other a donor group of formula (Xa), or (Xd); or R$^3$, R$^4$ and R$^6$ are H and R$^5$ is a donor group of formula (Xa), or (Xd); or R$^3$, R$^4$ and R$^5$ are H and R$^6$ is a donor group of formula (Xa), or (Xd).

Compounds of formula

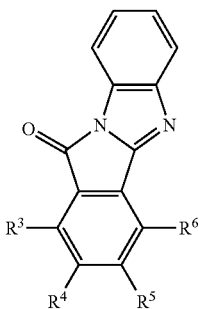
(IIb)

are even more preferred, wherein
$R^3$, $R^4$, $R^5$ and $R^6$ are independently of each other a donor group of formula (Xa), or (Xd); or
$R^3$ and $R^6$ are H and $R^4$ and $R^5$ are independently of each other a donor group of formula (Xa), or (Xd); or
$R^4$ and $R^5$ are H and $R^3$ and $R^6$ are independently of each other a donor group of formula (Xa), or (Xd); or
$R^3$, $R^4$ and $R^5$ are H and $R^6$ is a donor group of formula (Xa), or (Xd); or
$R^3$, $R^4$ and $R^6$ are H and $R^5$ is a donor group of formula (Xa), or (Xd); or
$R^3$, $R^5$ and $R^6$ are H and $R^4$ is a donor group of formula (Xa), or (Xd); or
$R^4$, $R^5$ and $R^6$ are H and $R^3$ is a donor group of formula (Xa), or (Xd).

Among the compounds of formula (III) compounds of formula

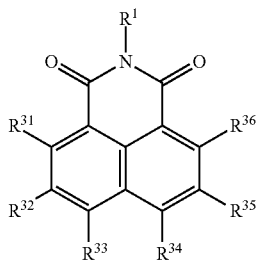
(IIIa), wherein $R^1$, $R^{31}$, $R^{32}$, $R^{33}$, $R^{34}$, $R^{35}$ and $R^{36}$ are as defined above, and

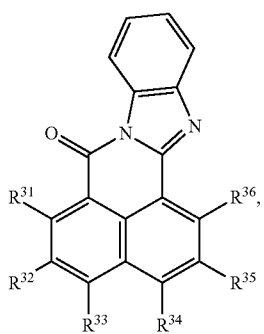
(IIIb)

wherein $R^{31}$, $R^{32}$, $R^{33}$, $R^{34}$, $R^{35}$ and $R^{36}$ are as defined above, are more preferred.

Compounds of formula

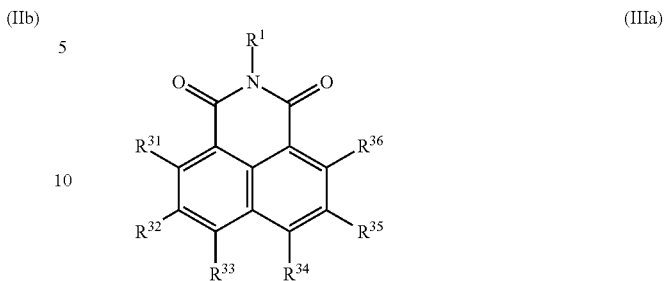
(IIIa)

are even more preferred, wherein
$R^{31}$, $R^{32}$, $R^{33}$, $R^{35}$ and $R^{36}$ are H and $R^{34}$ is a donor group of formula (Xa), or (Xd); or
$R^{31}$, $R^{32}$, $R^{33}$, $R^{34}$ and $R^{36}$ are H and $R^{35}$ is a donor group of formula (Xa), or (Xd); or
$R^{31}$, $R^{32}$, $R^{33}$, $R^{34}$ and $R^{35}$ are H and $R^{36}$ is a donor group of formula (Xa), or (Xd); or
$R^{31}$, $R^{32}$, $R^{35}$ and $R^{36}$ are H and $R^{33}$ and $R^{34}$ are independently of each other a donor group of formula (Xa), or (Xd);
$R^{32}$ and $R^{35}$ are H and $R^{31}$, $R^{33}$, $R^{34}$ and $R^{36}$ are independently of each other a donor group of formula (Xa), or (Xd); or
$R^{31}$, $R^{32}$, $R^{33}$, $R^{34}$, $R^{35}$ and $R^{36}$ are independently of each other a donor group of formula (Xa), or (Xd).

Compounds of formula

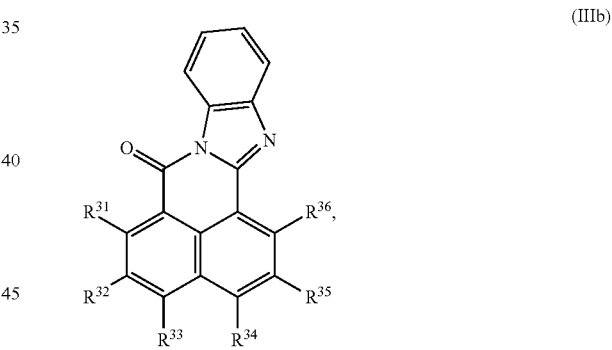
(IIIb)

are even more preferred, wherein
$R^{31}$, $R^{32}$, $R^{33}$, $R^{35}$ and $R^{36}$ are H and $R^{34}$ is a donor group of formula (Xa), or (Xd); or
$R^{31}$, $R^{32}$, $R^{34}$, $R^{35}$ and $R^{36}$ are H and $R^{33}$ is a donor group of formula (Xa), or (Xd); or
$R^{31}$, $R^{32}$, $R^{35}$ and $R^{36}$ are H and $R^{33}$ and $R^{34}$ are independently of each other a donor group of formula (Xa), or (Xd).

$R^1$ is preferably a $C_1$-$C_{25}$alkyl group, a group of formula

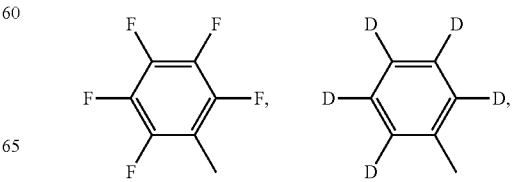

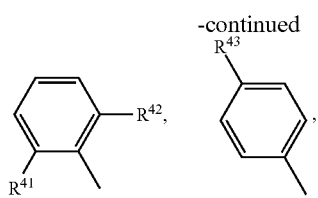

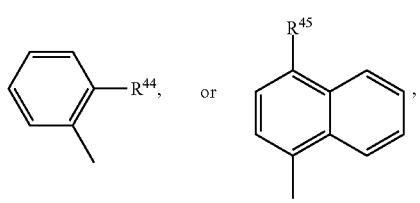

wherein
$R^{41}$ and $R^{42}$ are a $C_1$-$C_8$alkyl group;
$R^{43}$ is a $C_1$-$C_8$alkyl group, or a $C_1$-$C_8$alkoxy group;
$R^{44}$ is a $C_1$-$C_8$alkyl group, or a phenyl group; and
$R^{45}$ is a $C_1$-$C_8$alkyl group. More preferably, $R^1$ is a group of formula

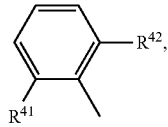

and $R^{42}$ are a $C_1$-$C_8$alkyl group.

The donor group is preferably a donor group of formula (Xa), wherein $X^1$ is a direct bond, O, S, $C(CH_3)(CH_3)$, $C(=O)$,

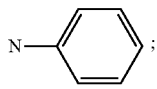

or a donor group of formula (Xd), wherein $R^{21}$ and $R^{21'}$ are H.

The donor group is more preferably a group of formula

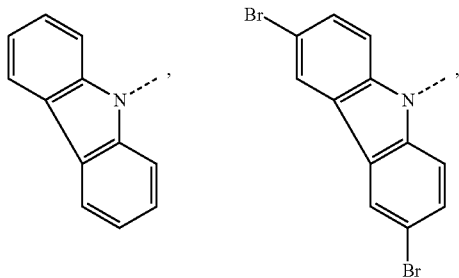

especially

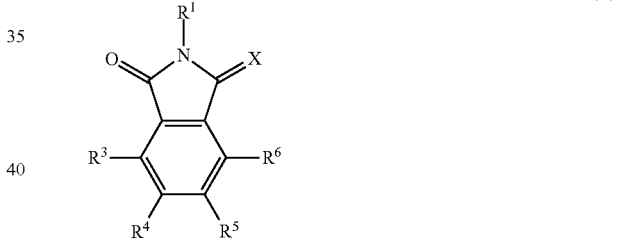

Examples of compounds of formula $$\text{(II)}$$

are shown below:

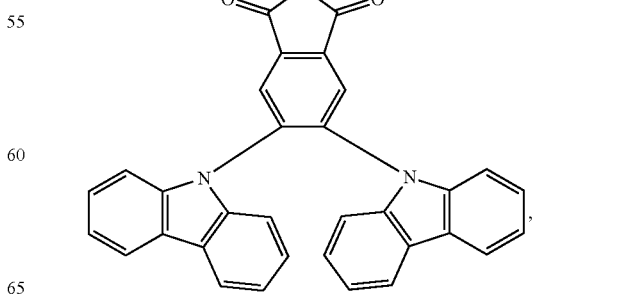

(A-1)

(A-2)
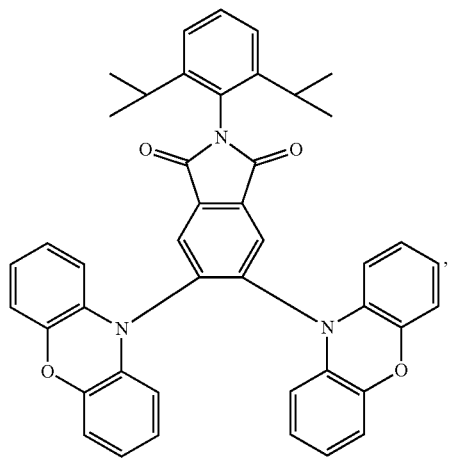
(A-3)
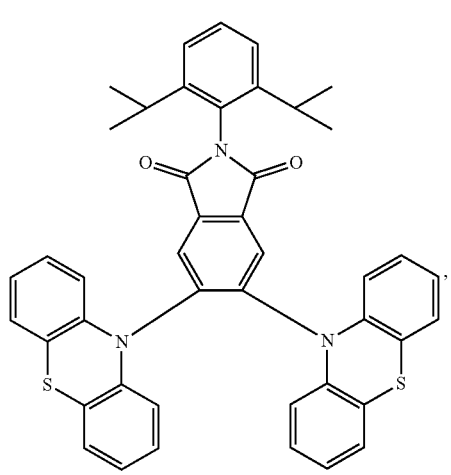
(A-4)
(A-5)
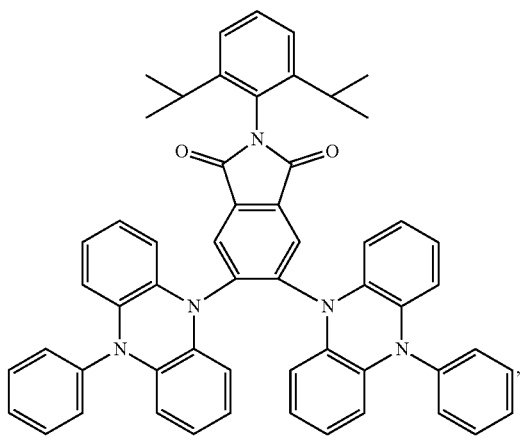
(A-6)
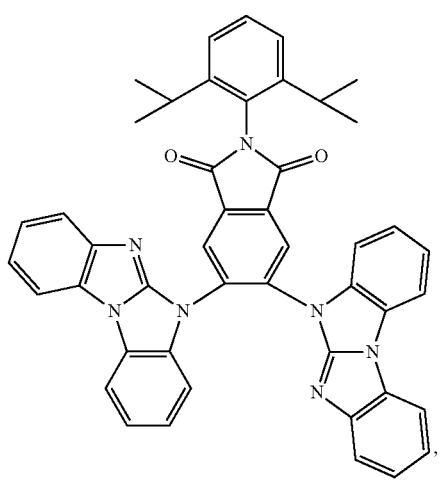
(A-7)
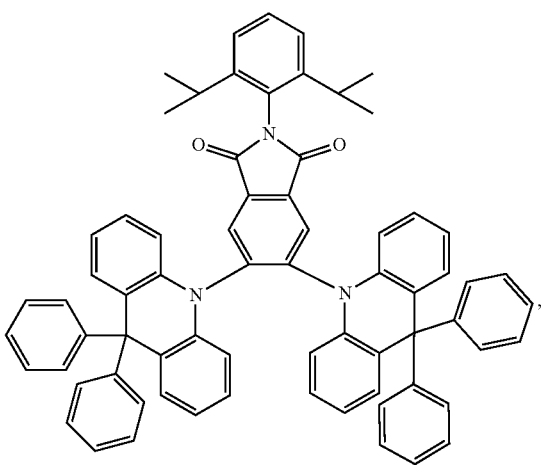

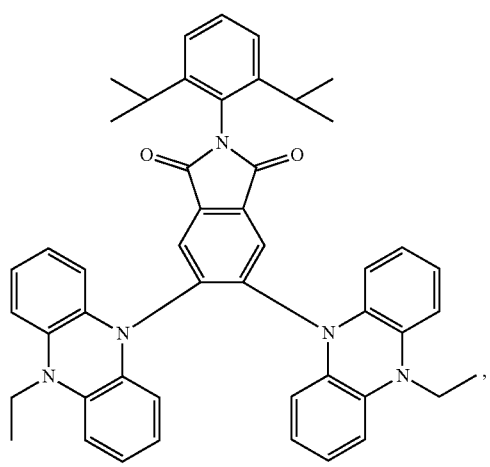
(A-8)
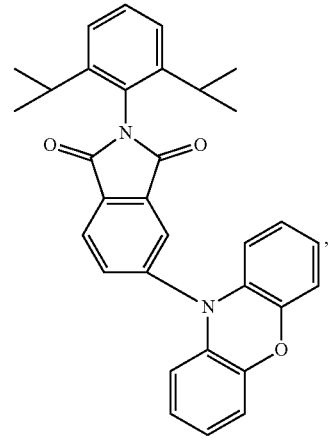
(A-11)
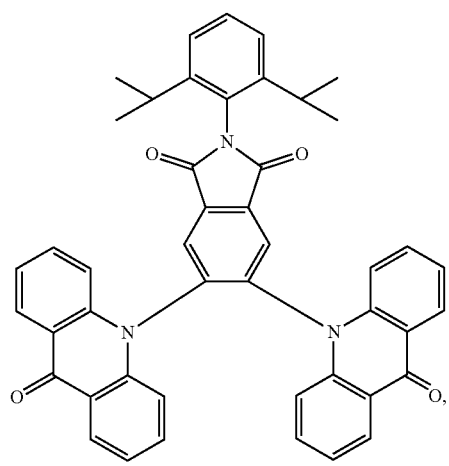
(A-9)
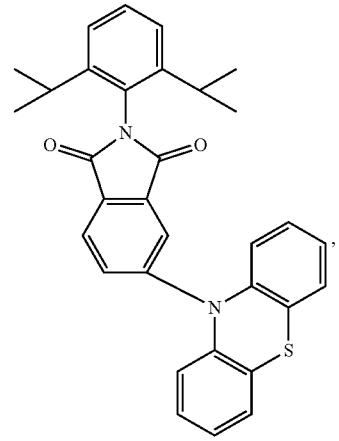
(A-12)
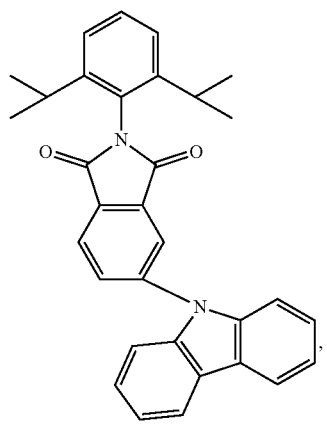
(A-10)
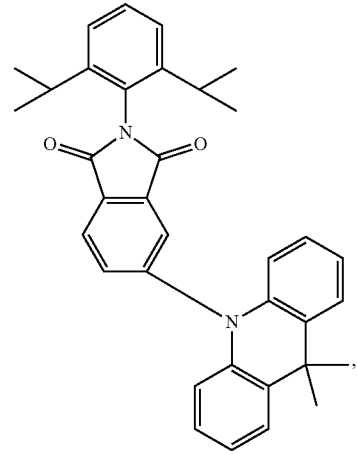
(A-13)

(A-14)
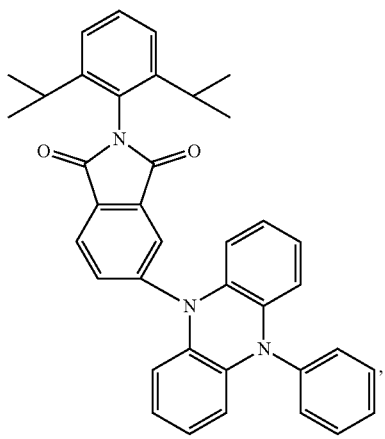
(A-17)
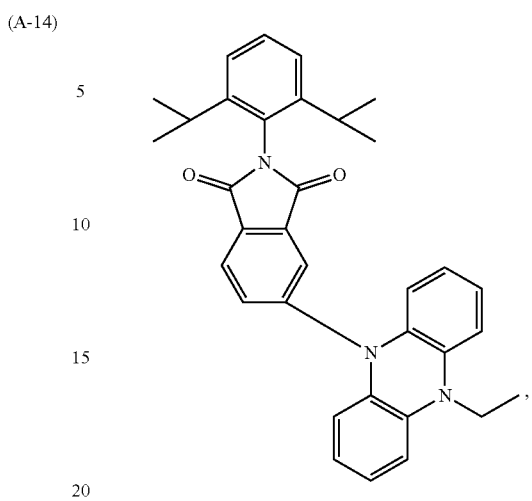
(A-15)
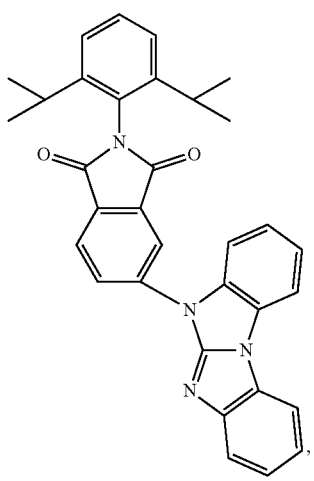
(A-18)
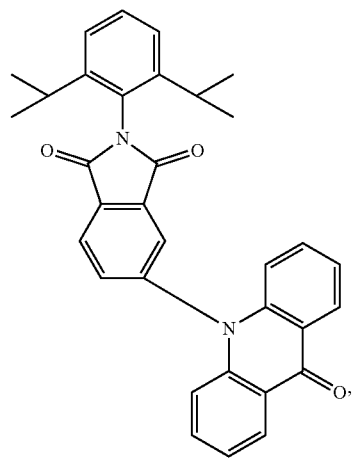
(A-16)
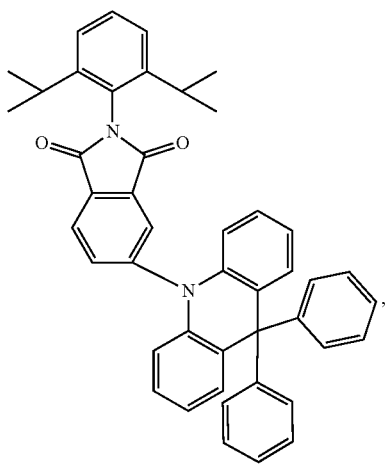
(A-19)
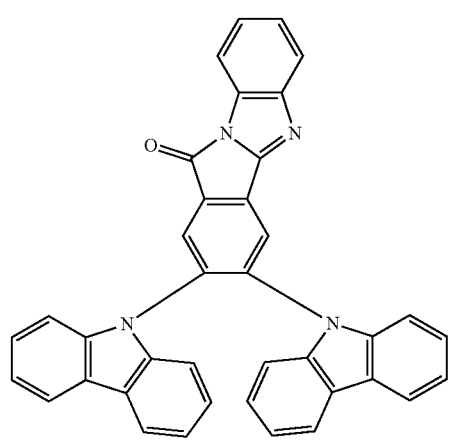

(A-20)
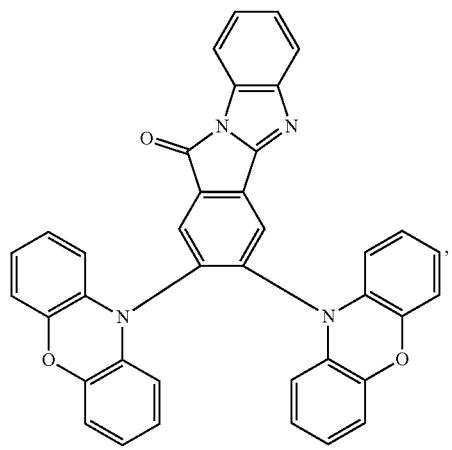
(A-23)
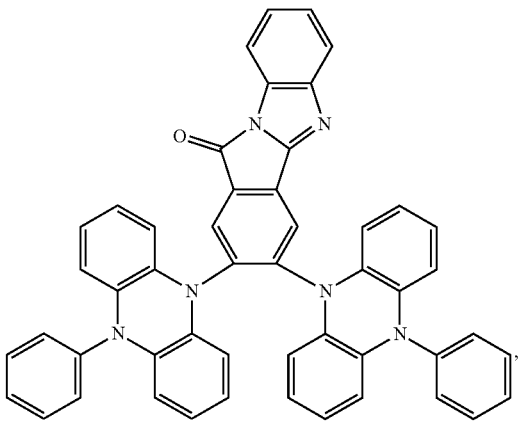
(A-21)
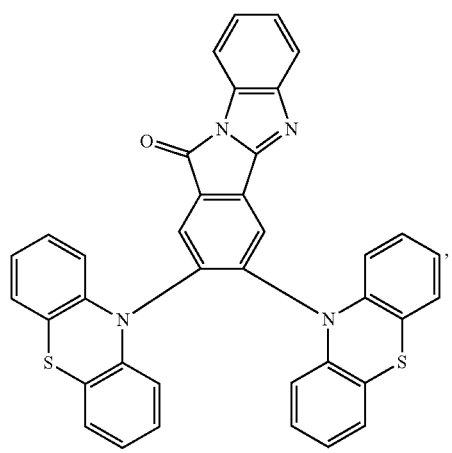
(A-24)
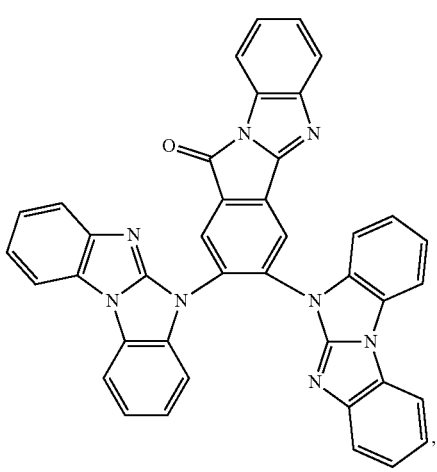
(A-22)
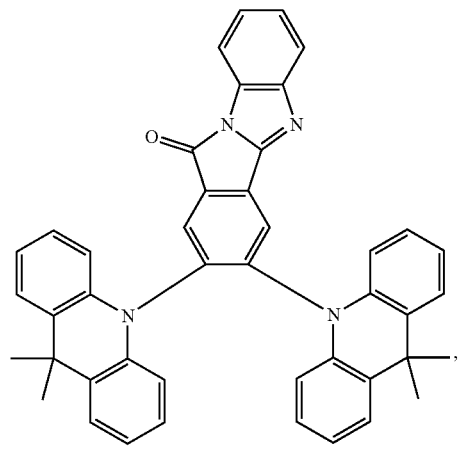
(A-25)

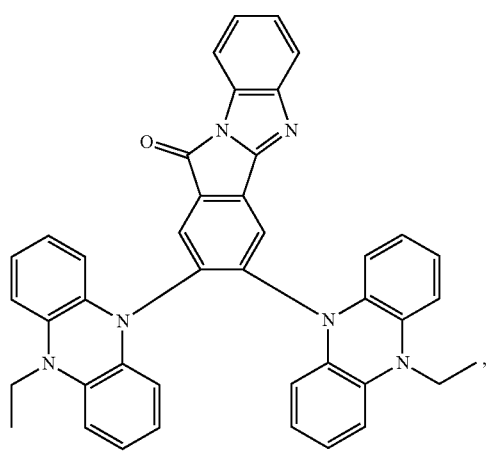
(A-26)
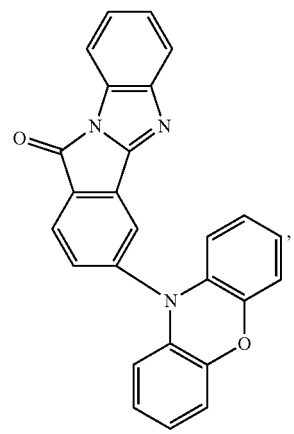
(A-29)
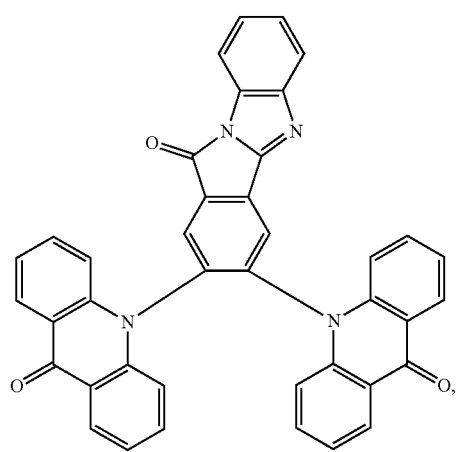
(A-27)
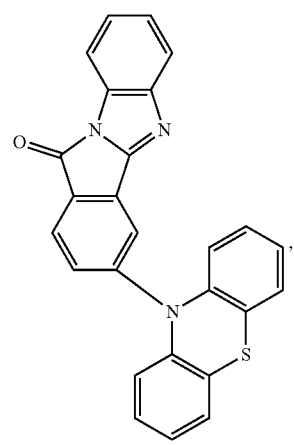
(A-30)
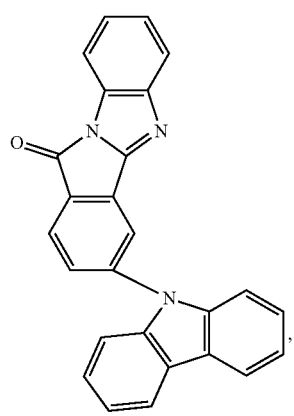
(A-28)
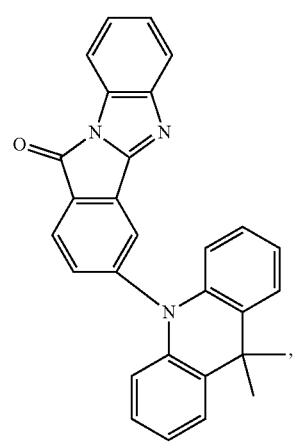
(A-31)

(A-32)
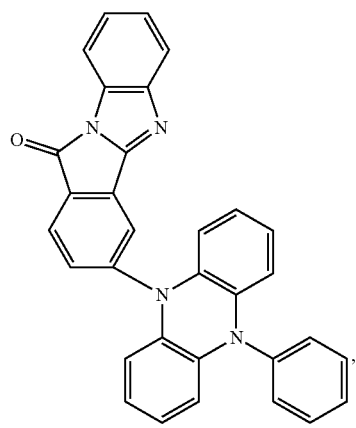
(A-33)
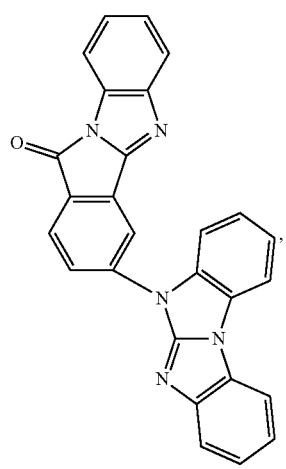
(A-34)
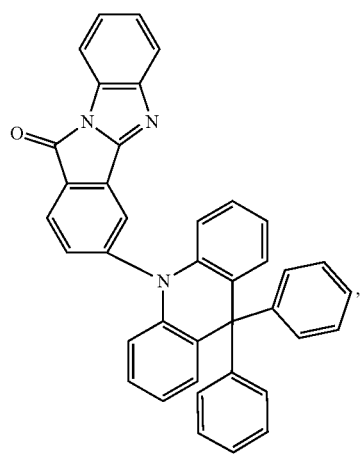
(A-35)
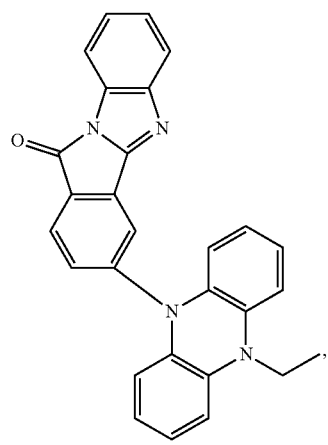
(A-36)
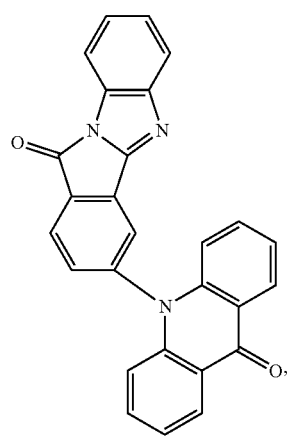
(A-37)
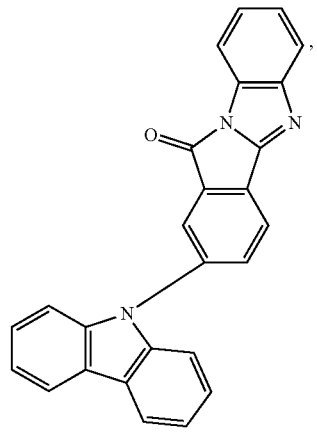

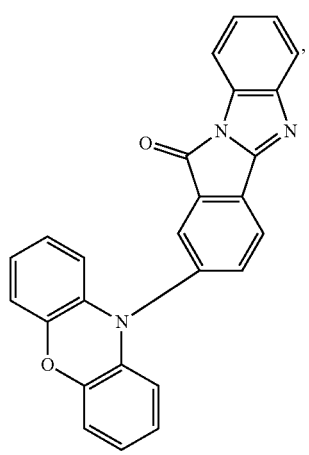 (A-38)
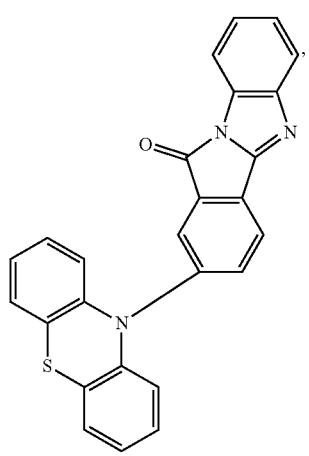 (A-39)
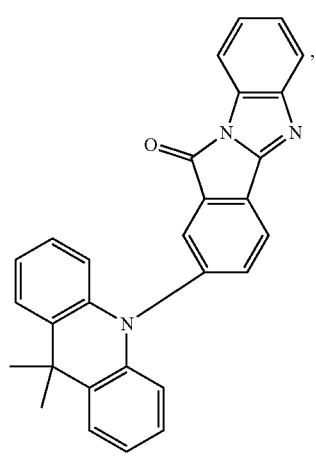 (A-40)
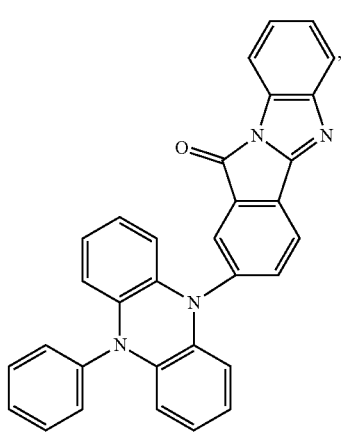 (A-41)
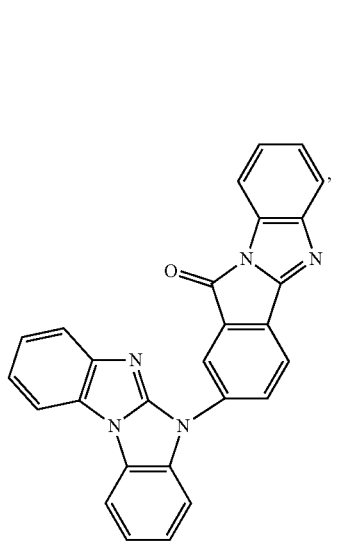 (A-42)
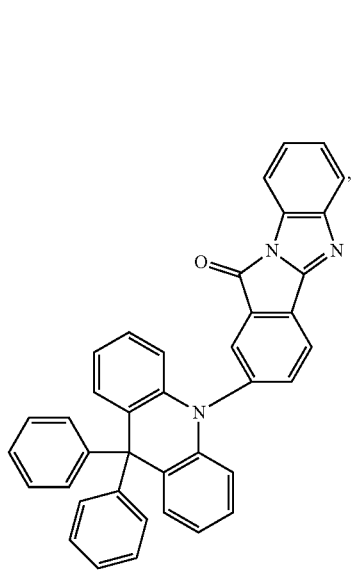 (A-43)

(A-44)
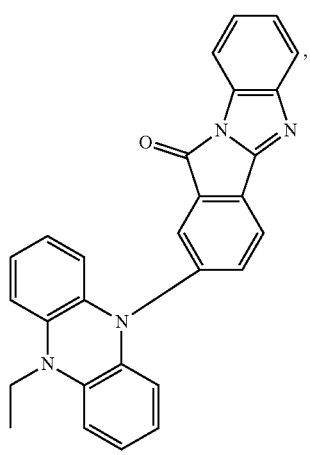
(A-45)
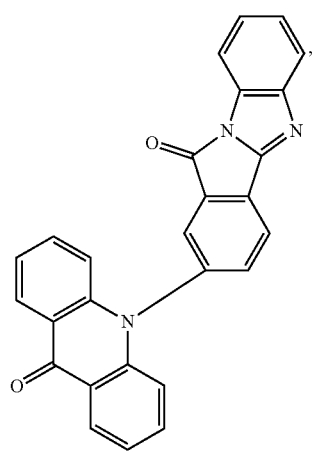
(A-46)
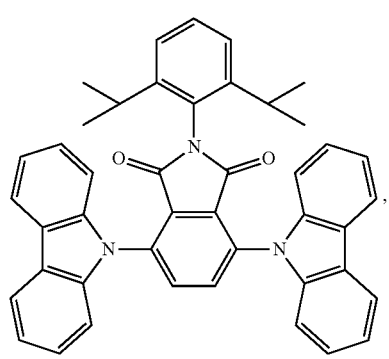
(A-47)
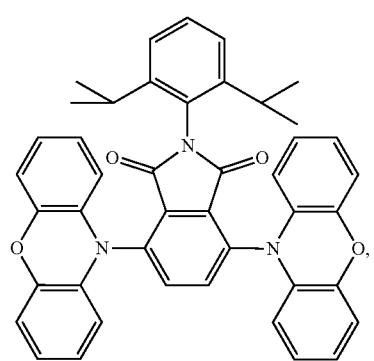
(A-48)
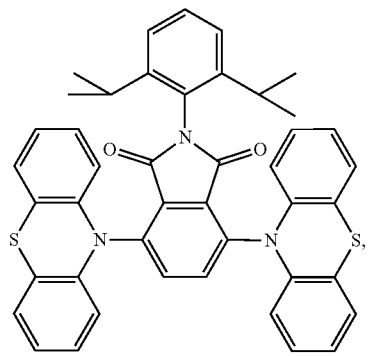
(A-49)
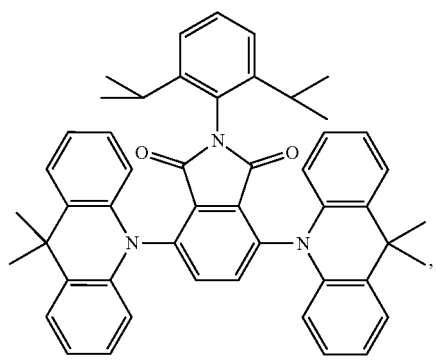
(A-50)
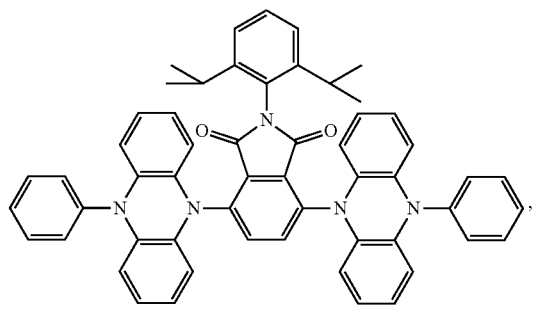
(A-51)
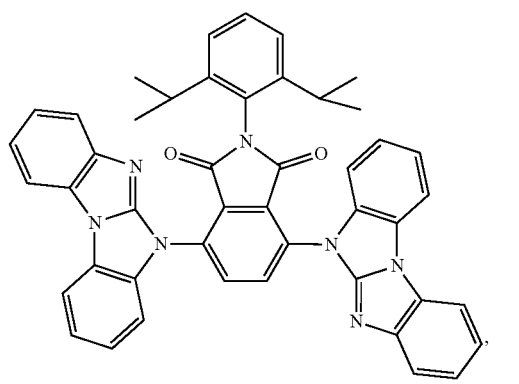

(A-52)
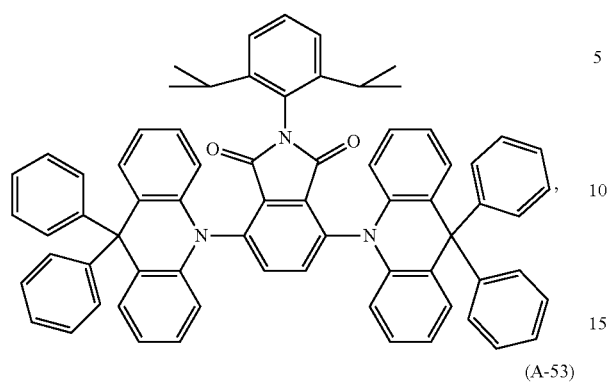
(A-53)
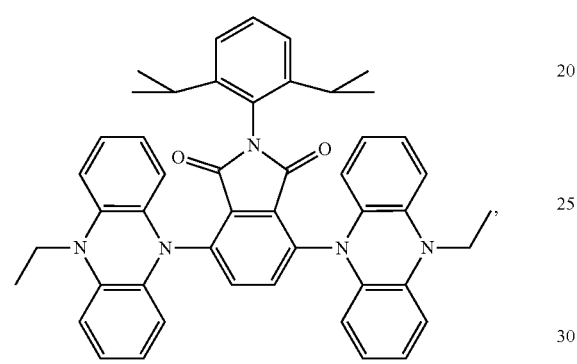
(A-54)
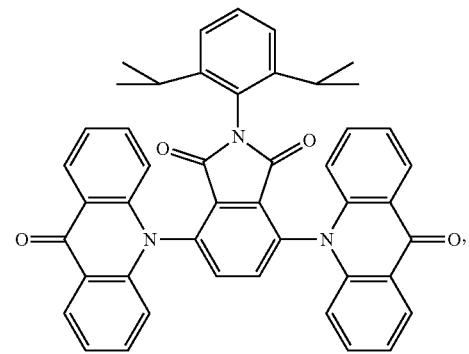
(A-55)
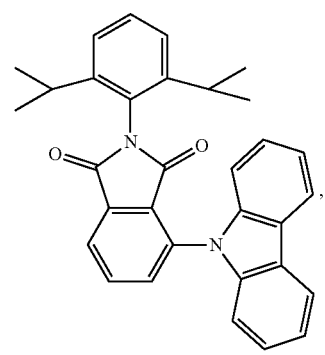
(A-56)
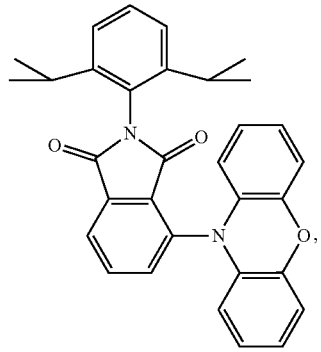
(A-57)
(A-58)
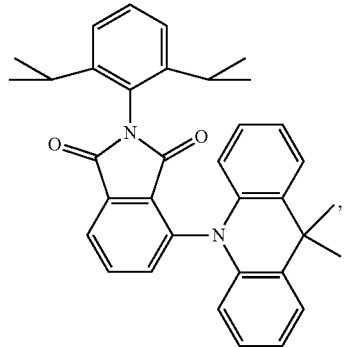
(A-59)

(A-60)
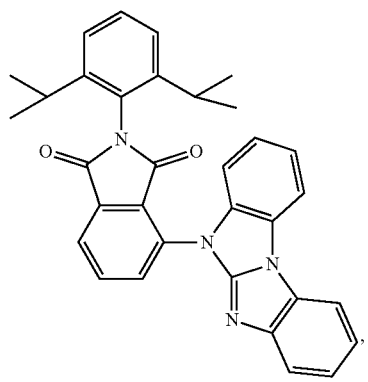
(A-61)
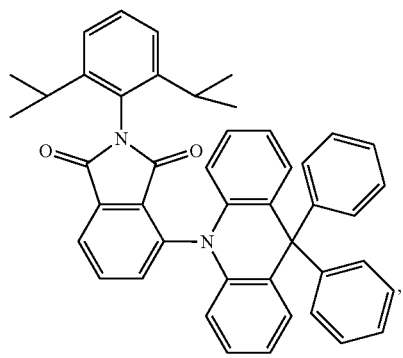
(A-62)
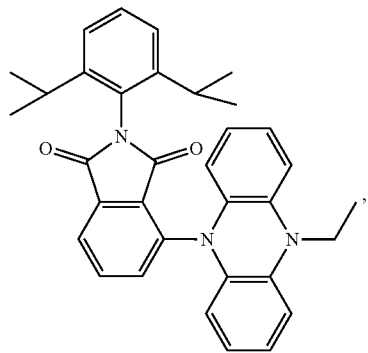
(A-63)
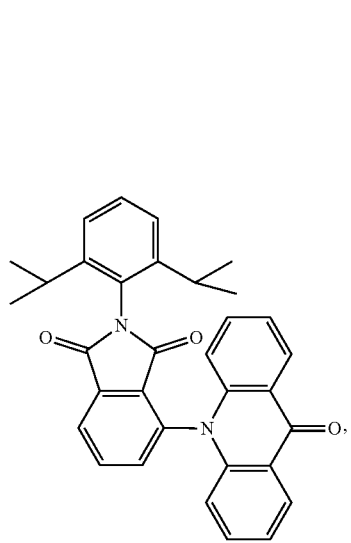
(A-64)
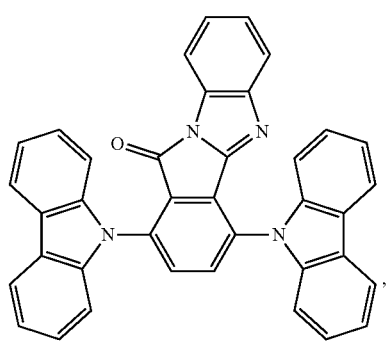
(A-65)
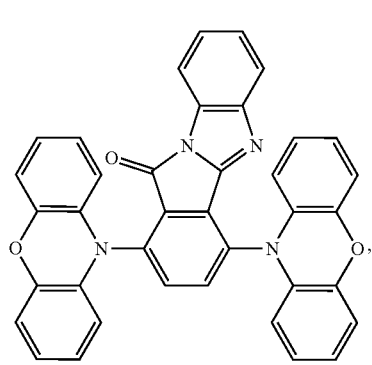
(A-66)
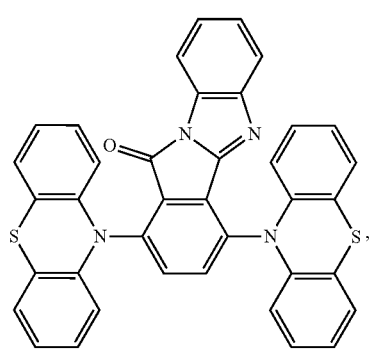
(A-67)
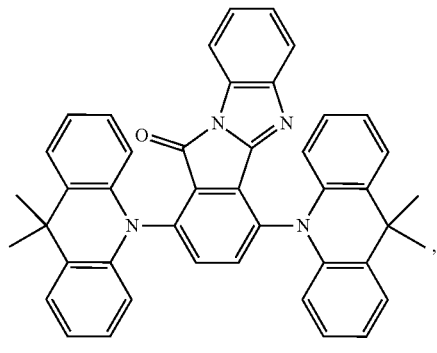

-continued
(A-68)
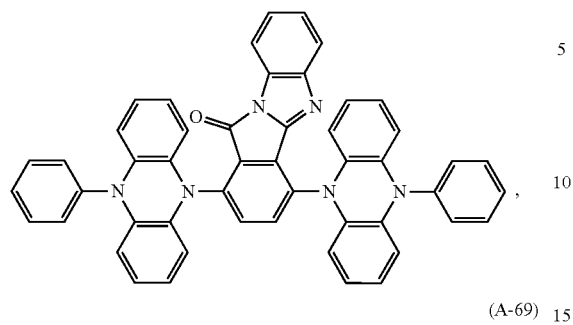
(A-69)
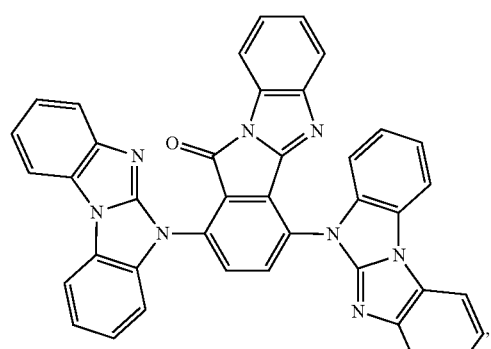
(A-70)
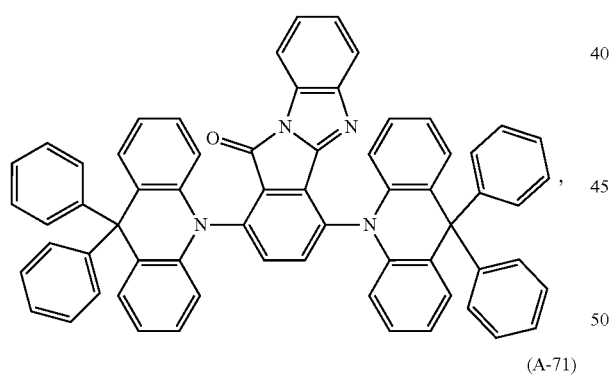
(A-71)
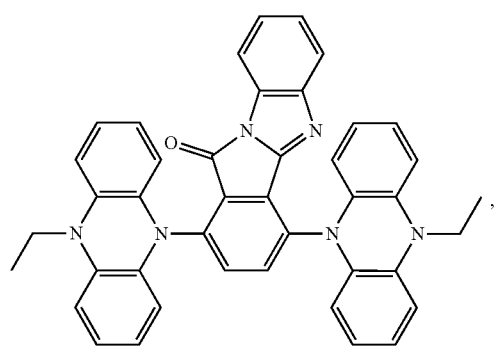
-continued
(A-72)
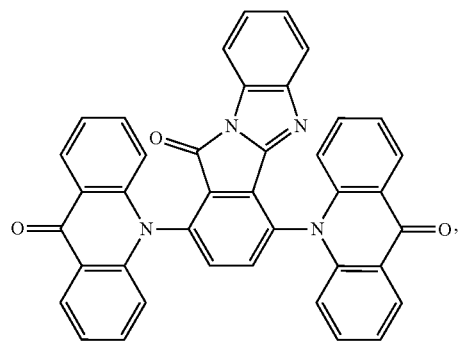
(A-73)
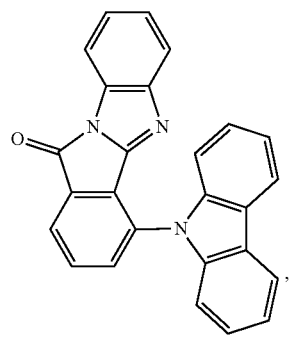
(A-74)
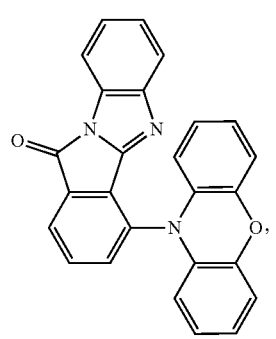
(A-75)
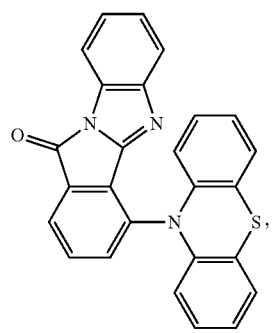

-continued
(A-76)
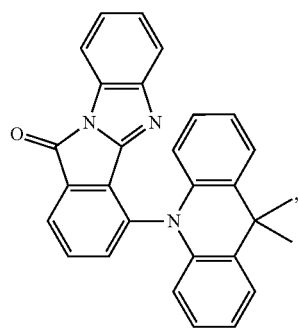
(A-77)
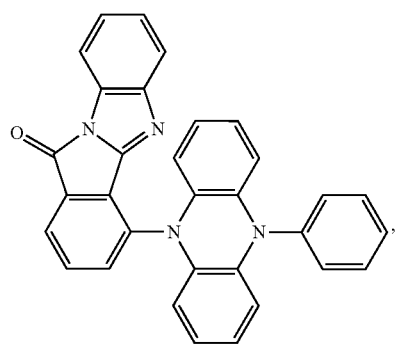
(A-78)
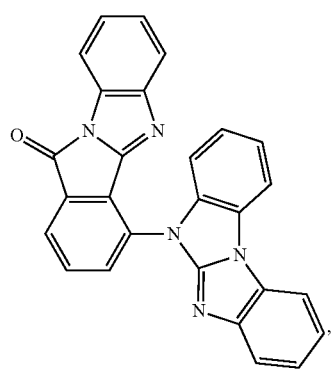
(A-79)
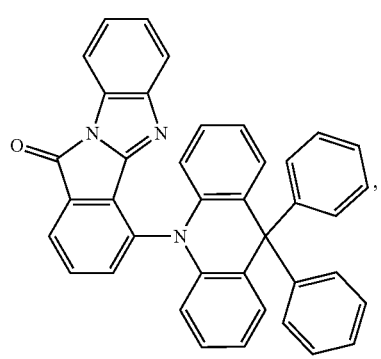
-continued
(A-80)
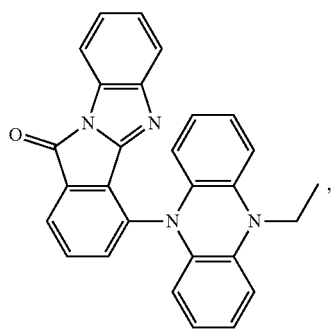
(A-81)
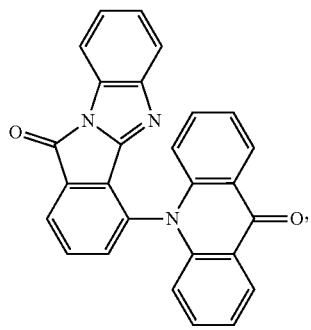
(A-82)
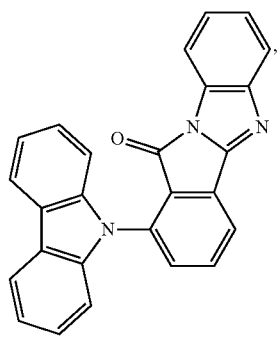
(A-83)
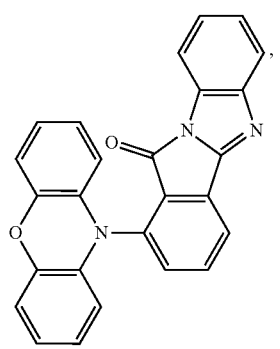

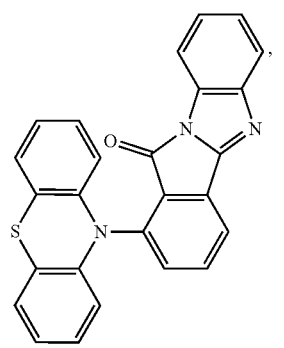
(A-84)
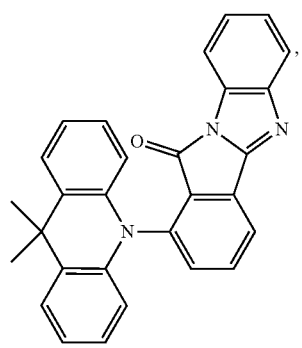
(A-85)
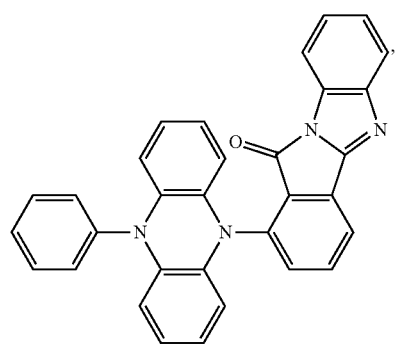
(A-86)
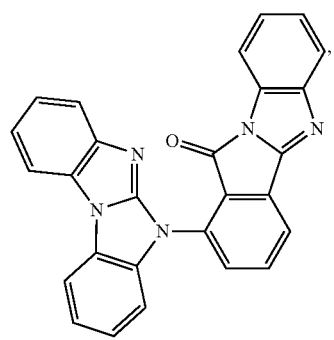
(A-87)
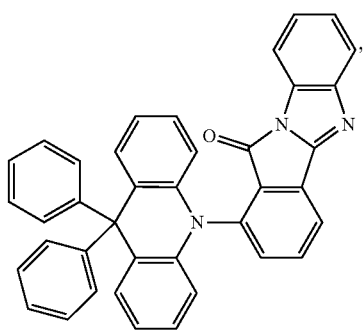
(A-88)
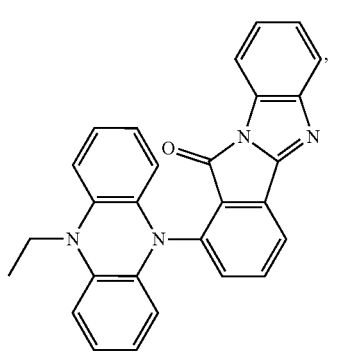
(A-89)
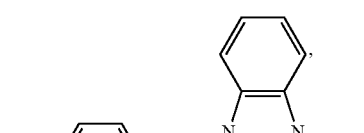
(A-90)
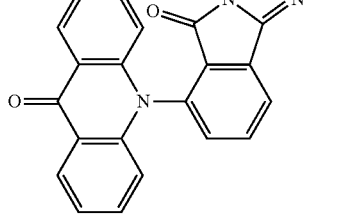
(A-91)

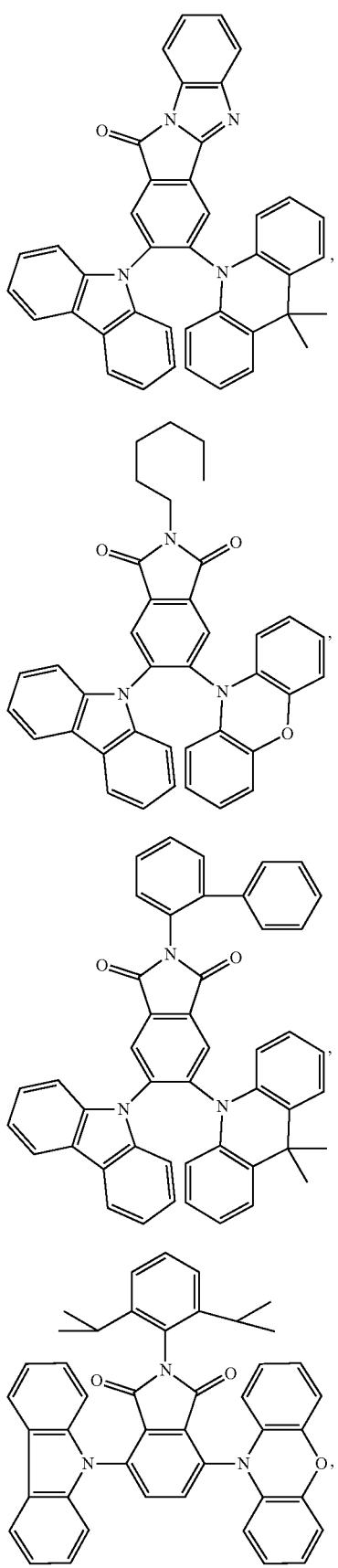
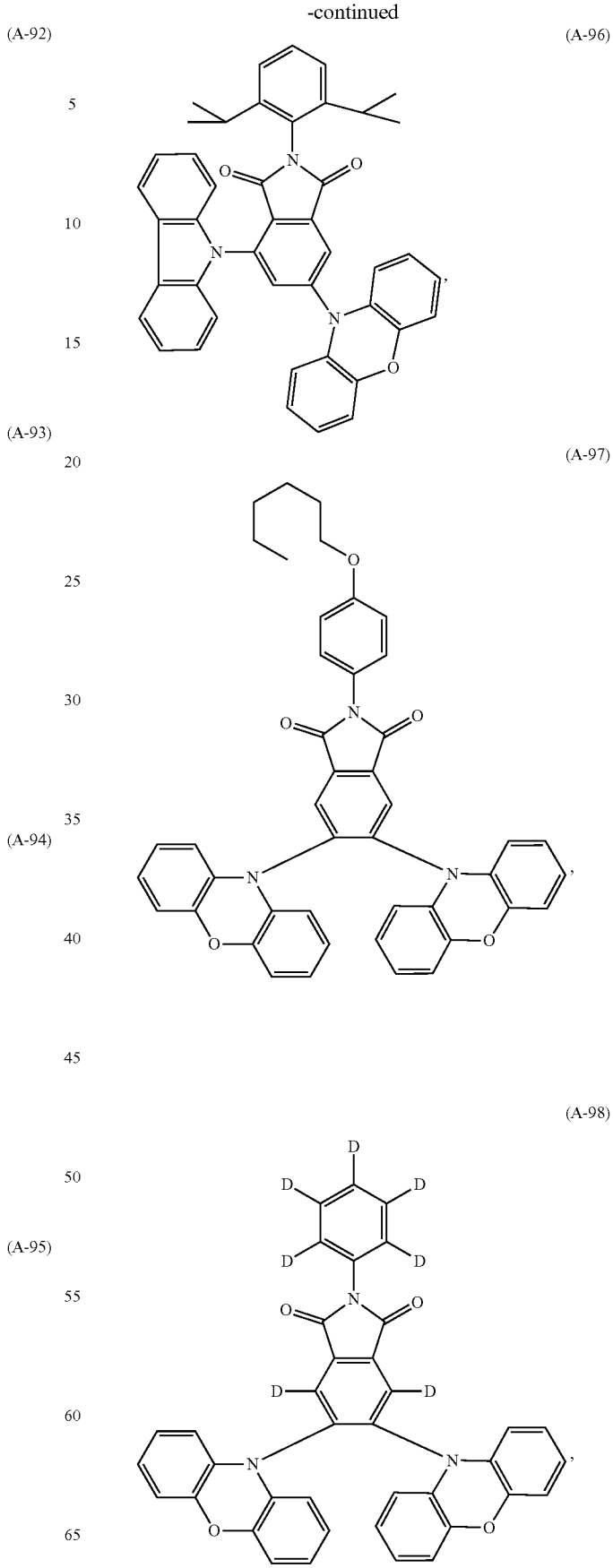

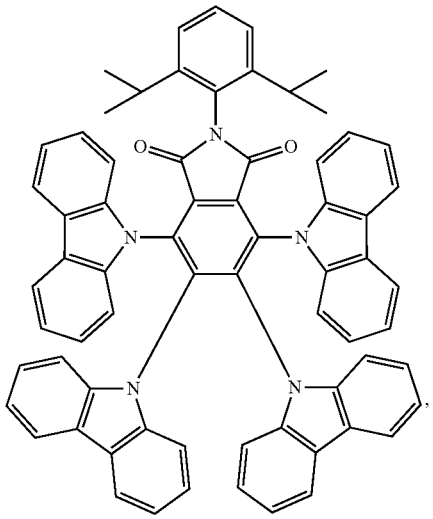

(A-99)

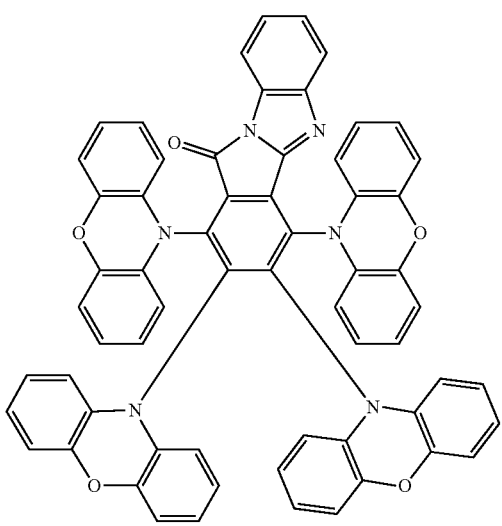

(A-100)

Among compounds of formula (H) those are preferred which are substituted especially by donor groups of formula

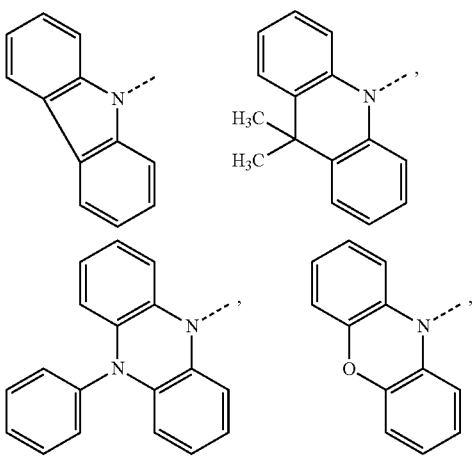

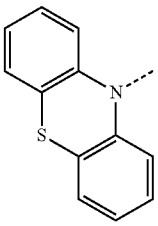 and 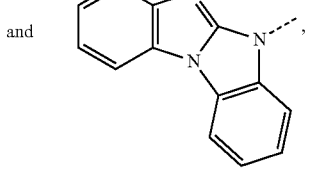, such as, for example, compounds (A-1), (A-2), (A-3), (A-4), (A-5), (A-6), (A-10), (A-11), (A-12), (A-13), (A-14), (A-15), (A-19), (A-20), (A-21), (A-22), (A-23), (A-24), (A-28), (A-29), (A-30), (A-31), (A-32), (A-33), (A-37), (A-38), (A-39), (A-40), (A-41), (A-42), (A-46), (A-47), (A-48), (A-49), (A-50), (A-51), (A-55), (A-56), (A-57), (A-58), (A-59), (A-60), (A-64), (A-65), (A-66), (A-67), (A-68), (A-69), (A-73), (A-74), (A-75), (A-76), (A-77), (A-78), (A-82), (A-83), (A-84), (A-85), (A-86), (A-87), (A-92), (A-93) (A-94), (A-95), (A-96), (A-97), (A-99), and (A-100).

The most preferred examples are (A-1), (A-2), (A-3), (A-4), (A-6), (A-10), (A-11), (A-12), (A-13), (A-15), (A-19), (A-20), (A-21), (A-22), (A-24), (A-28), (A-29), (A-30), (A-31), (A-33), (A-37), (A-38), (A-39), (A-40), (A-42), (A-46), (A-47), (A-48), (A-49), (A-51), (A-55), (A-56), (A-57), (A-58), (A-60), (A-64), (A-65), (A-66), (A-67), (A-69), (A-73), (A-74), (A-75), (A-76), (A-78), (A-82), (A-83), (A-84), (A-85), (A-87), (A-92), (A-99), and (A-100).

Examples of compounds of formula

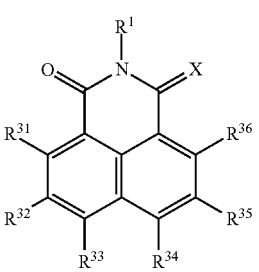 (III)

are shown below:

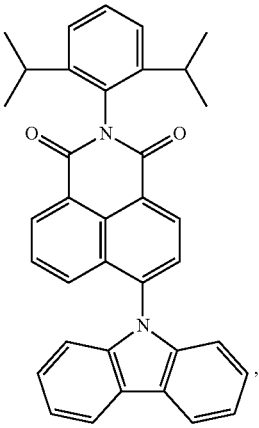 (B-1)

(B-2)
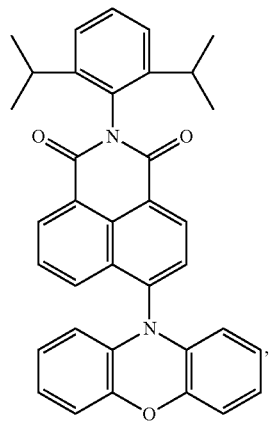
(B-3)
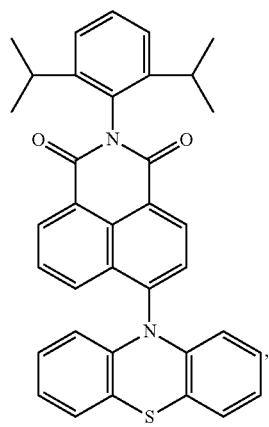
(B-4)
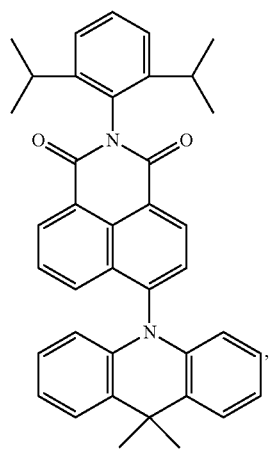
(B-5)
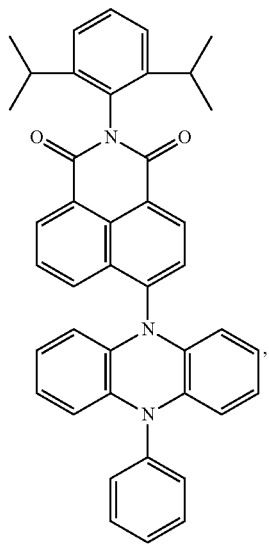
(B-6)
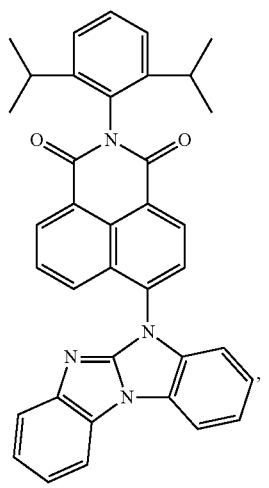
(B-7)
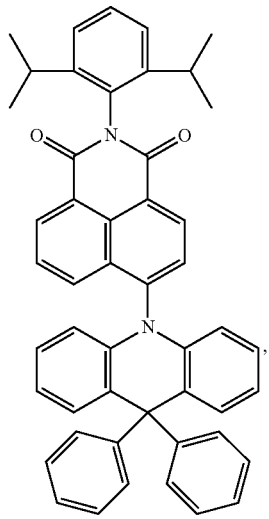

(B-8)
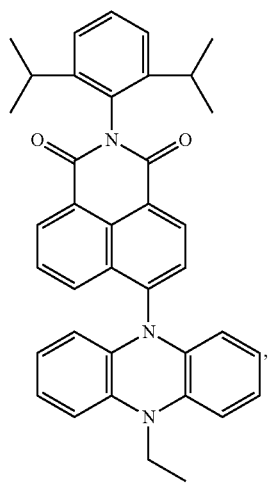
(B-9)
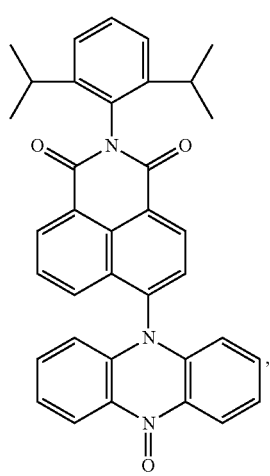
(B-10)
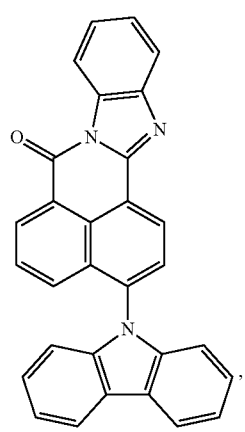
(B-11)
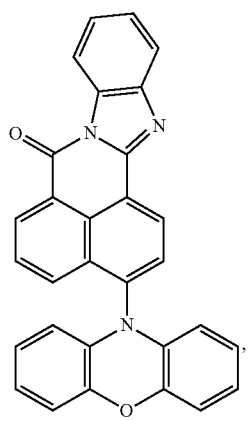
(B-12)
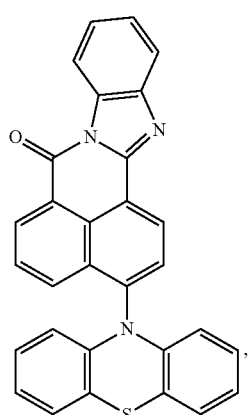
(B-13)
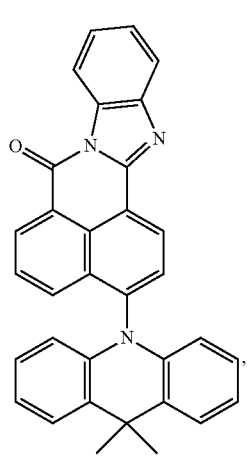

(B-14)

(B-15)

(B-16)

(B-17)

(B-18)

(B-19)

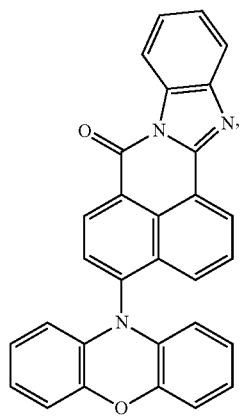
(B-20)
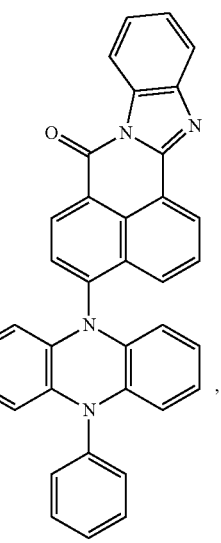
(B-23)
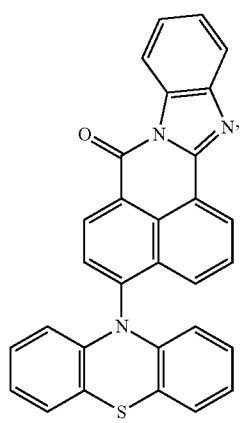
(B-21)
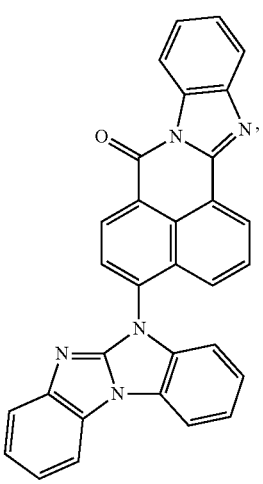
(B-24)
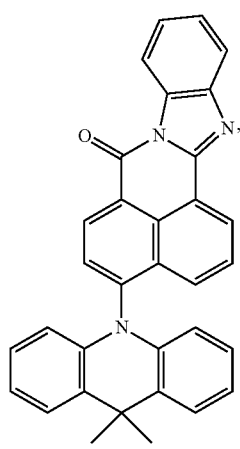
(B-22)
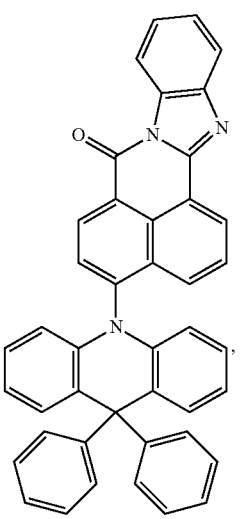
(B-25)

(B-26) 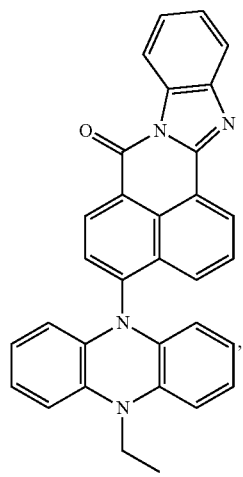
(B-27) 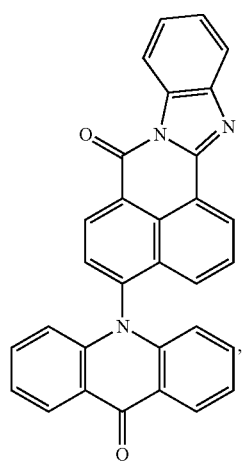
(B-28) 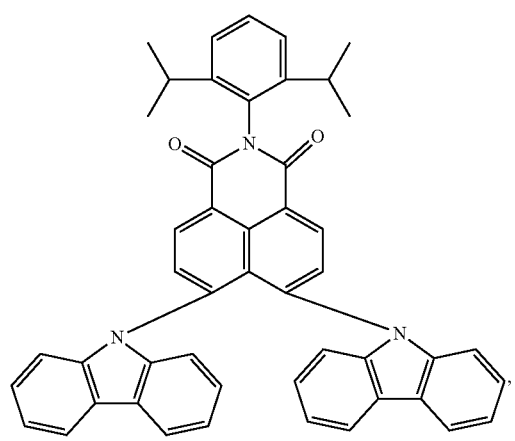
(B-29) 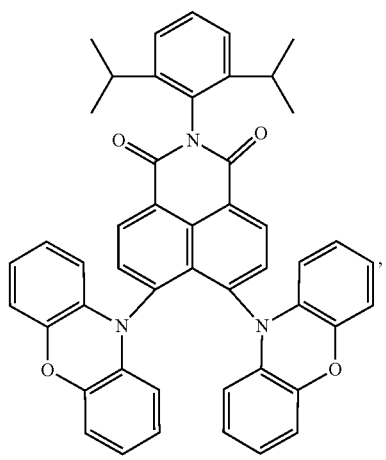
(B-30) 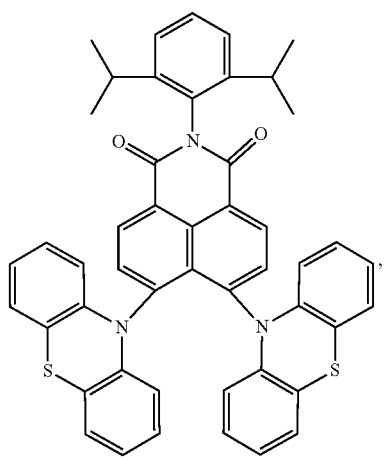
(B-31) 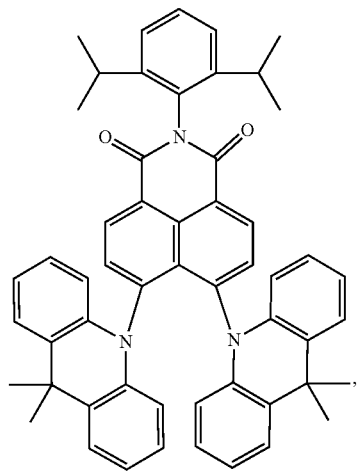

(B-32)
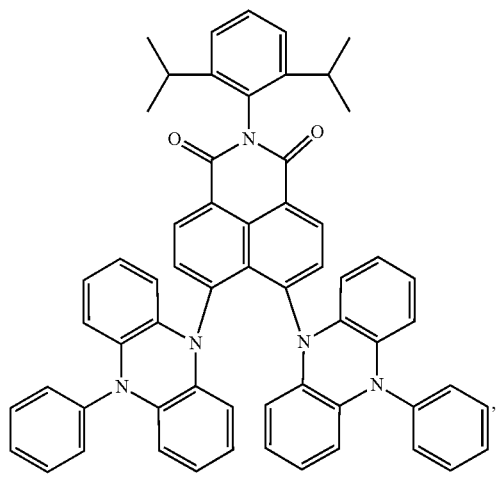
(B-33)
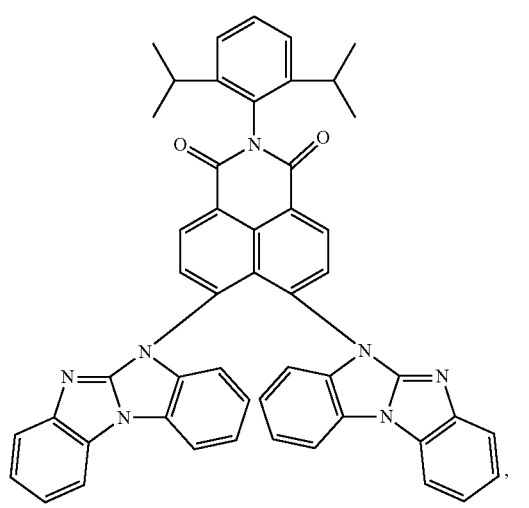
(B-34)
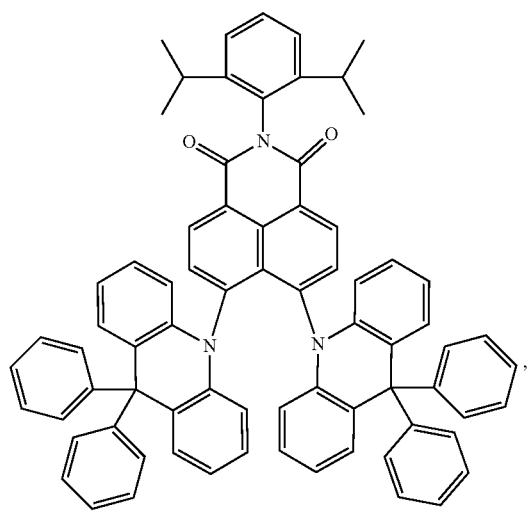
(B-35)
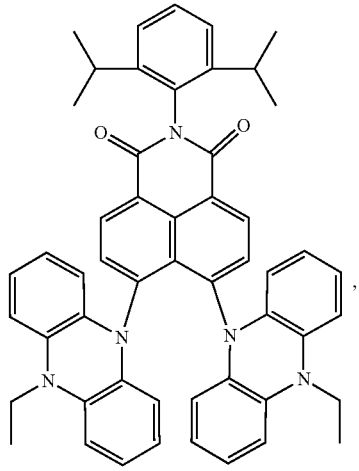
(B-36)
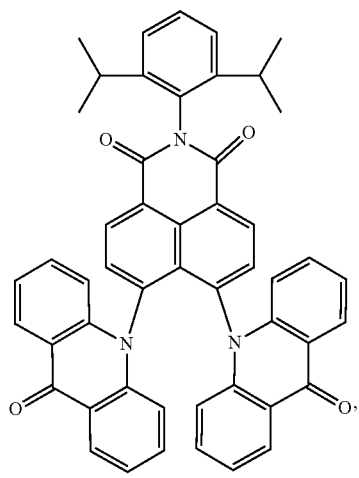
(B-37)
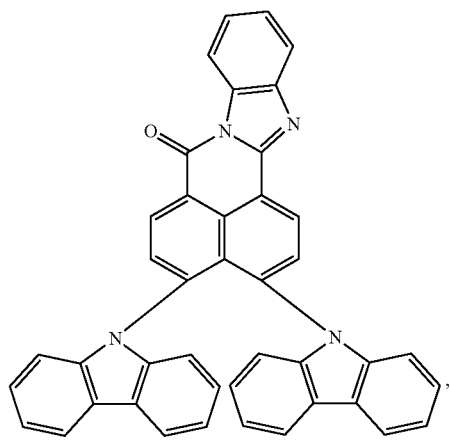

(B-38)
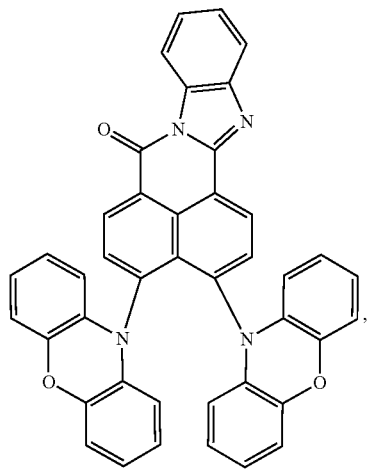
(B-39)
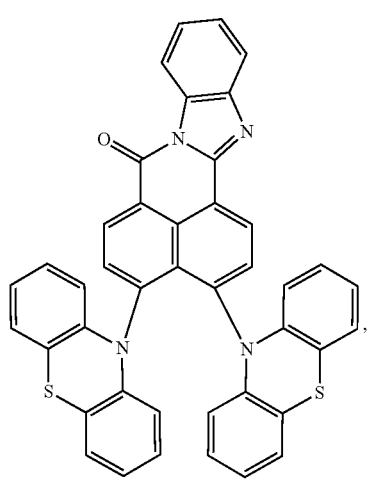
(B-40)
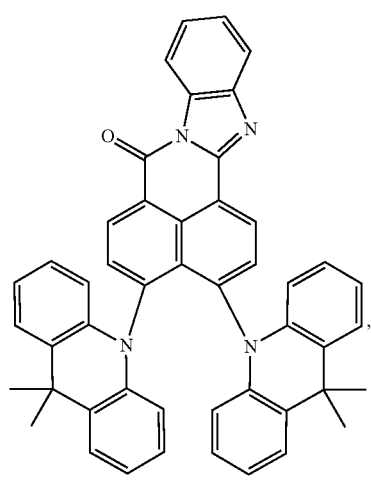
(B-41)
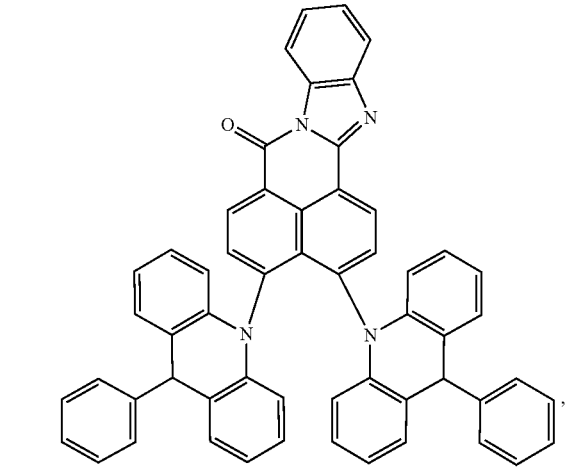
(B-42)
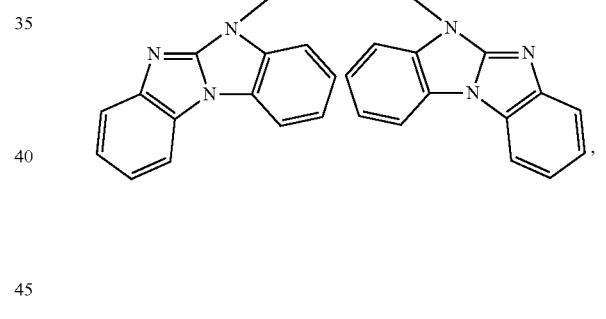
(B-43)
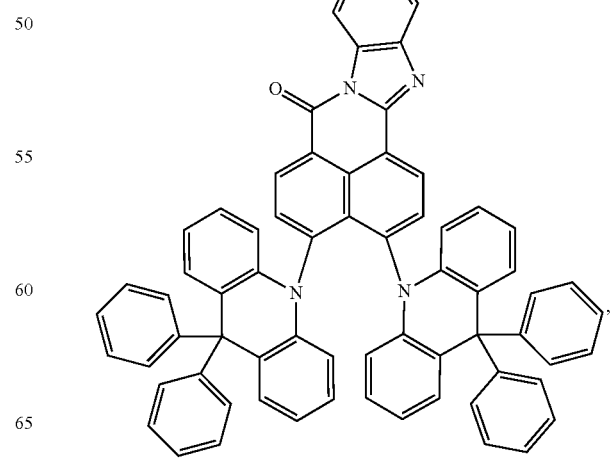

(B-44)
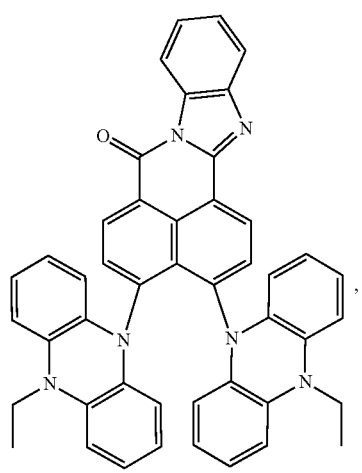
(B-45)
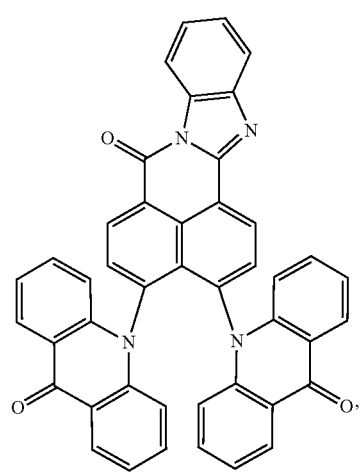
(B-46)
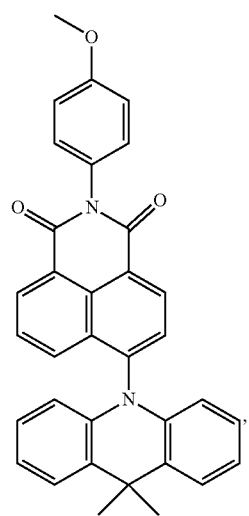
(B-47)
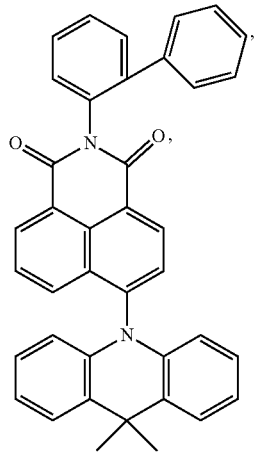
(B-48)
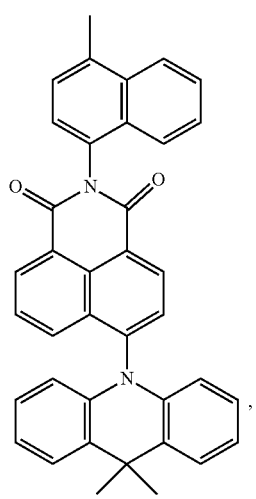
(B-49)
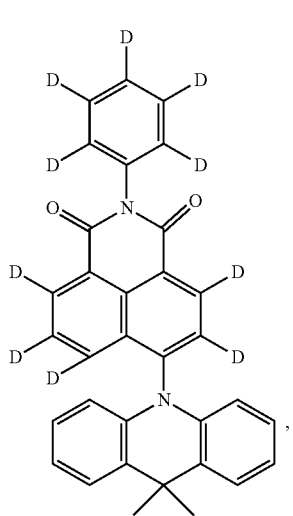

(B-50)
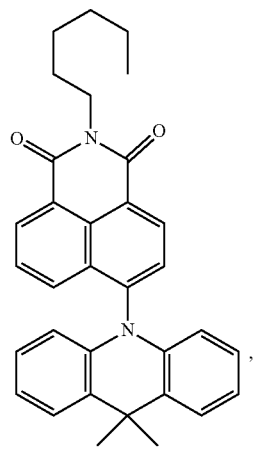
(B-51)
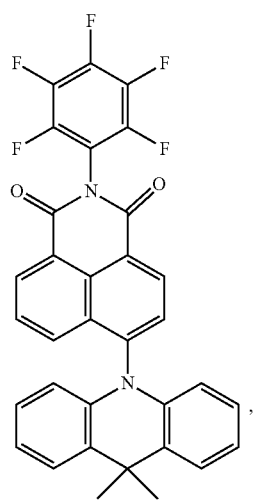
(B-52)
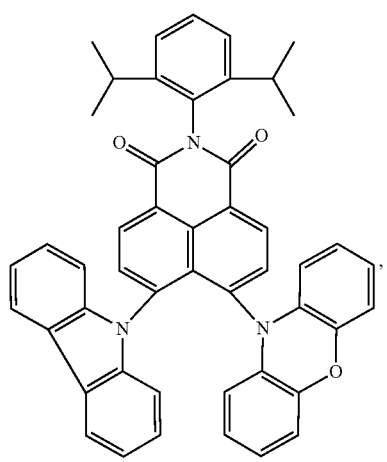
(B-53)
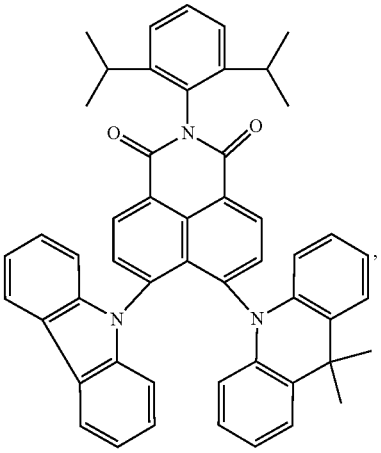
(B-54)
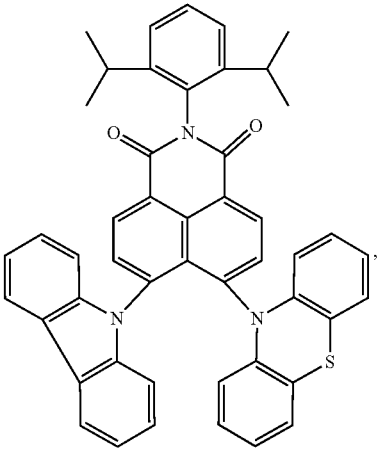
(B-55)
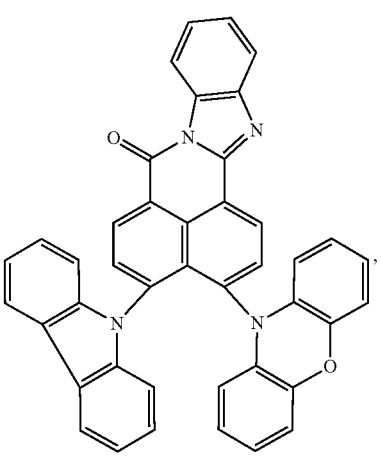

(B-56)
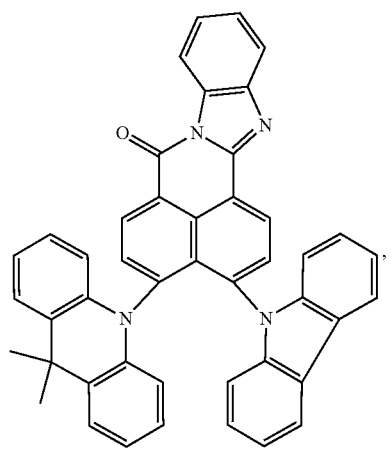
(B-57)
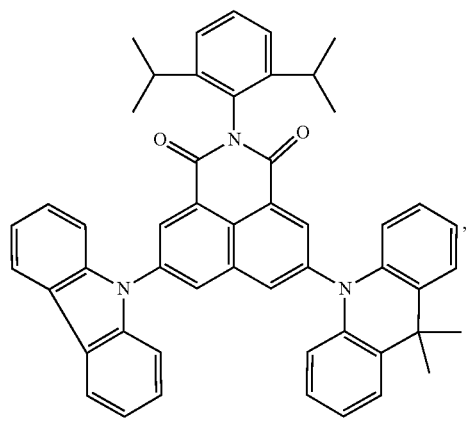
(B-58)
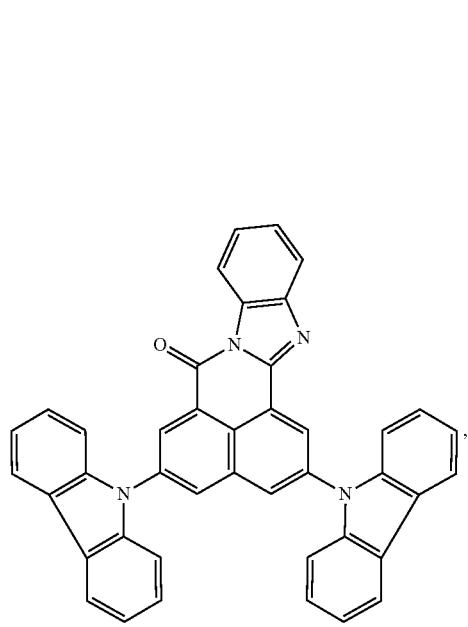
(B-59)
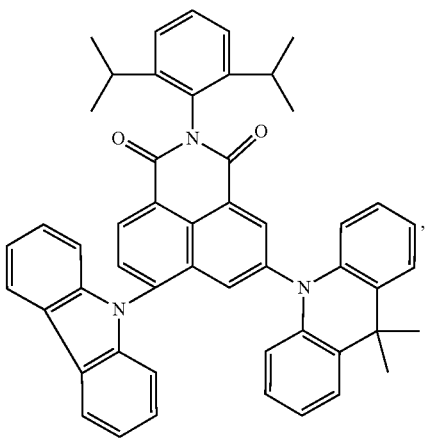
(B-60)
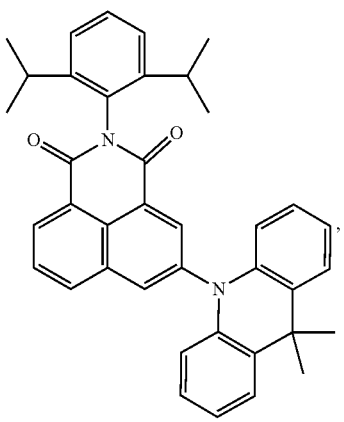
(B-61)
(B-62)
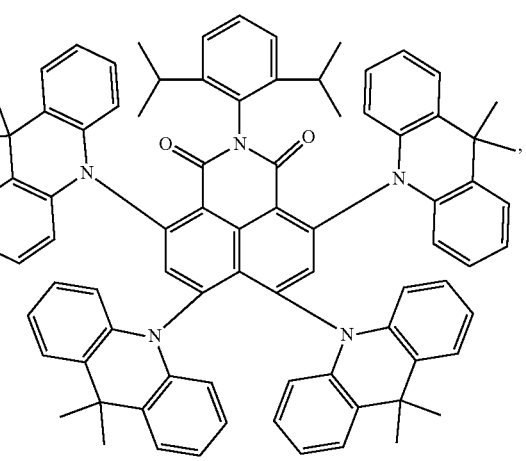

-continued (B-63)

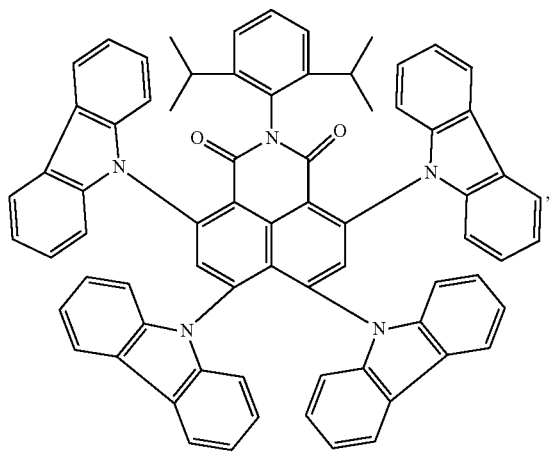

(B-64)

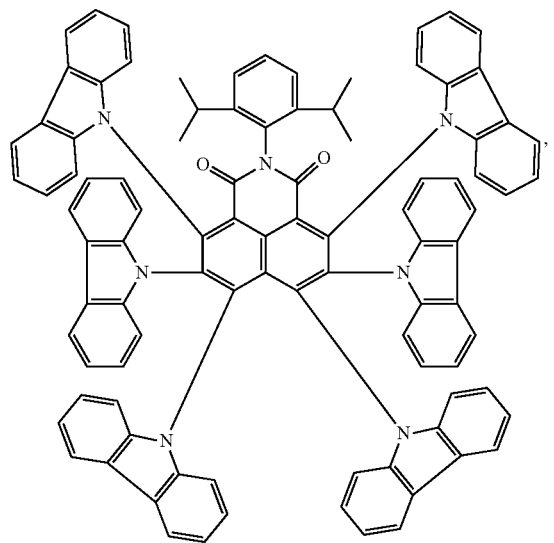

Among compounds of formula (III) those are preferred which are substituted especially by donor groups of formula

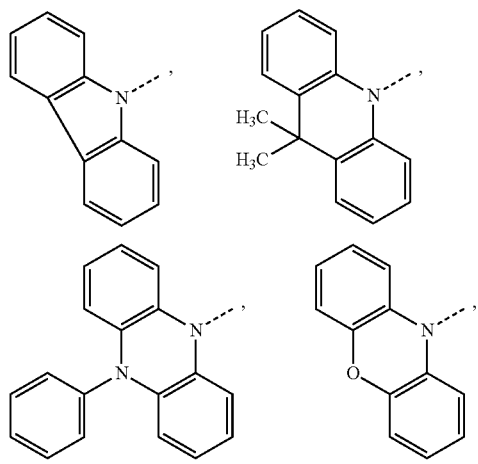

-continued

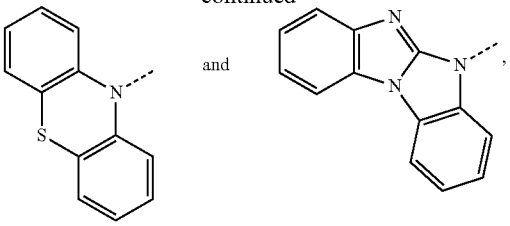

such as, for example, compounds (B-1), (B-2), (B-3), (B-4), (B-5), (B-6), (B-10), (B-11), (B-12), (B-13), (B-14), (B-15), (B-19), (B-20), (B-21), (B-22), (B-23), (B-24), (B-28), (B-29), (B-30), (B-31), (B-32), (B-33), (B-37), (B-38), (B-39), (B-40), (B-41), (B-42), (B-46), (B-47), (B-48), (B-49), (B-50), (B-51), (B-52), (B-53), (B-54), (B-55), (B-56), (B-57), (B-58), (B-59), (B-60), (B-61), (B-62), (B-63) and (B-64).

The most preferred examples are (B-1), (B-4), (B-6), (B-10), (B-13), (B-15), (B-19), (B-20), (B-21), (B-23), (B-24), (B-28), (B-29), (B-31), (B-33), (B-37), (B-38), (B-39), (B-40), (B-42), (B-52), (B-53), (B-55), (B-56), (B-57), (B-58), (B-59), (B-60), (B-61), (B-62), and (B-63).

$C_1$-$C_{25}$alkyl, $C_1$-$C_{18}$alkyl and $C_1$-$C_{12}$alkyl, respectively is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_6$alkyl is typically methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl and n-hexyl.

$C_2$-$C_4$alkenyl groups are straight-chain or branched alkenyl groups, such as e.g. vinyl, allyl, methallyl, isopropenyl, 2-butenyl and 3-butenyl.

$C_1$-$C_{25}$alkoxy groups, $C_1$-$C_{18}$alkoxy groups and $C_1$-$C_{12}$alkoxy groups, respectively are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

$C_6$-$C_{14}$aryl, especially $C_6$-$C_{10}$aryl, which optionally can be substituted, is typically phenyl, naphthyl, especially 1-naphthyl, or 2-naphthyl, or biphenylyl, which may be unsubstituted or substituted by one, or more $C_1$-$C_8$alkyl, $C_1$-$C_8$alkoxy and/or $C_6$-$C_{10}$aryloxy groups, especially $C_1$-$C_8$alkyl, $C_1$-$C_8$alkoxy groups.

$C_6$-$C_{10}$aryloxy, which optionally can be substituted by one, or more $C_1$-$C_8$alkyl and/or $C_1$-$C_8$alkoxy groups, is typically phenoxy, 1-naphthoxy, or 2-naphthoxy.

The present invention is directed to a light-emitting layer comprising the compound of the formula (I).

In addition, the present invention is directed to an organic light emitting element, comprising the compound of the formula (I).

For the compounds of formula (I) the preferences specified above apply.

Compounds of formula (II) and (III) are preferred. Compounds of formula (IIa), (IIb), (IIIa) and (IIIb) are more preferred. Among compounds of formula (IIa), (IIb), (IIIa) and (IIIb) compounds (A-1) to (A-100) and (B-1) to (B-64) are preferred, compounds (A-1), (A-2), (A-3), (A-4), (A-6), (A-10), (A-11), (A-12), (A-13), (A-15), (A-19), (A-20), (A-21), (A-22), (A-24), (A-28), (A-29), (A-30), (A-31), (A-33), (A-37), (A-38), (A-39), (A-40), (A-42), (A-46), (A-47), (A-48), (A-49), (A-51), (A-55), (A-56), (A-57), (A-58), (A-60), (A-64), (A-65), (A-66), (A-67), (A-69), (A-73), (A-74), (A-75), (A-76), (A-78), (A-82), (A-83), (A-84), (A-85), (A-87), (A-92), (A-99), (A-100), (B-1), (B-4), (B-6), (B-10), (B-13), (B-15), (B-19), (B-20), (B-21), (B-23), (B-24), (B-28), (B-29), (B-31), (B-33), (B-37), (B-38), (B-39), (B-40), (B-42), (B-52), (B-53), (B-55), (B-56), (B-57), (B-58), (B-59), (B-60), (B-61), (B-62) and (B-63) are most preferred.

The compounds of formula (I) can be used as host in combination with a fluorescent guest material in the emitting layer of an organic EL element. Known fluorescent materials are usable as the fluorescent guest material. Examples of the fluorescent guest material include a bisarylamino naphthalene derivative, an aryl-substituted naphthalene derivative, a bisarylamino anthracene derivative, an aryl-substituted anthracene derivative, a bisarylamino pyrene derivative, an aryl-substituted pyrene derivative, a bisarylamino chrysene derivative, an aryl-substituted chrysene derivative, a bisarylamino fluoranthene derivative, an aryl-substituted fluoranthene derivative, an indenoperylene derivative, a pyrromethene boron complex compound, a compound having a pyrromethene skeleton or a metal complex thereof, a diketopyrrolopyrrole derivative, and a perylene derivative. Examples are 2,5,8,11-tetra-tert-butylperylene (TBPe), 9,10-bis[N,N-di-(p-tolyl)-amino]anthracene (TTPA), 2,8-di-tert-butyl-5,11-bis(4-tert-butylphenyl)-6,12-diphenyltetracene (TBRb) and dibenzo{[f,f']-4,4',7,7'-tetraphenyl}diindeno[1,2,3-cd:1',2',3'-lm]perylene (DBP). In case of using the compound of formula (I) as host material, the content of the compound of formula (I) in the light-emitting layer falls within the range of 51 to 99 wt %, preferably 80 to 99 wt %.

Alternatively, the compounds of formula (I) can be used as guest in combination with a host material in the emitting layer of an organic EL element. In said embodiment the compound of formula (I), i.e. the organic light-emitting material, has preferably a difference between excited singlet energy and excited triplet energy (($\Delta E_{ST}$)) of 0.5 eV or less, more preferably $\Delta E_{ST}$ of 0.35 eV or less, i.e. of 0.01 to 0.5 eV, especially 0.01 to 0.35 eV. The organic light-emitting material may be used alone in the light-emitting layer. However, as necessary, for the purpose of, for example, confining, in the organic light-emitting material, singlet excitons and triplet excitons generated in the organic light-emitting material, the organic light-emitting material of the present invention and an organic compound which has a higher value of at least any one of excited singlet energy and excited triplet energy than those of the organic light-emitting material and serves as a host material are preferably used in the light-emitting layer. At least any one of the excited singlet energy ($S_{1h}$) and excited triplet energy ($T_{1h}$) of the host compound is preferably higher by 0.1 eV or more, particularly preferably higher by 0.2 eV or more than the excited singlet energy ($S_{1g}$) and excited triplet energy ($T_{1g}$) of the organic light-emitting material of the present invention. That is, it is preferred that one or both of ($S_{1h}$)−($S_{1g}$)>0.1 eV and ($T_{1h}$)−($T_{1g}$)>0.1 eV be satisfied and it is more preferred that one or both of ($S_{1h}$)−($S_{1g}$)>0.2 eV and ($T_{1h}$)−($T_{1g}$)>0.2 eV be satisfied.

The organic EL element of the present invention has, as essential layers, an anode, a hole-transporting layer, a light-emitting layer, and a cathode.

Further, the organic EL element of the present invention may have, as layers other than the essential layers, an electron-transporting layer, an electron-injecting layer, an electron-blocking layer, a hole-blocking layer, and an exciton element layer. In addition, the hole-transporting layer may be a hole-injecting/transporting layer having a hole-injecting function and the electron-transporting layer may be an electron-injecting/transporting layer having an electron-injecting function.

The organic EL element of the present invention may comprise in this order: a substrate, an anode, a hole-injecting layer, a hole-transporting layer, a light-emitting layer, an electron-transporting layer and a cathode. Alternatively, the cathode, the electron-transporting layer, the light-emitting layer, the hole-transporting layer, and the anode may be laminated on the substrate in the stated order.

Substrate

The organic EL element of the present invention is preferably supported by a substrate. The substrate is not particularly limited and may be any substrate which is conventionally used in an organic EL element. For example, a substrate formed of glass, transparent plastic, quartz, or the like may be used.

Anode

Preferably used as the anode in the organic EL element is one using, as an electrode substance, any of a metal, an alloy, an electrically conductive compound, and a mixture thereof with a high work function (4 eV or more). Specific examples of such electrode substance include metals such as Au and conductive transparent materials such as CuI, indium tin oxide (ITO), $SnO_2$, and ZnO. Further, a material capable of producing an amorphous transparent conductive film such as IDIXO ($In_2O_3$—ZnO) may be used. In the production of the anode, it is possible to form any of those electrode substances into a thin film by a method such as vapor deposition or sputtering, and then form a pattern having a desired shape by a photolithographic method. Alternatively, in the case of using a coatable substance such as an organic conductive compound, it is also possible to employ a wet film-forming method of a printing mode, a coating mode, or the like.

Cathode

Meanwhile, used as the cathode is one using, as an electrode substance, any of a metal (referred to as electron-injecting metal), an alloy, an electrically conductive compound, and a mixture thereof with a low work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, from the viewpoints of electron-injecting property and durability against oxidation and the like, a mixture of an electron-injecting metal and a second metal, which has a work function value higher than that of the electron-injecting metal and is a stable metal, such as a magnesium/silver mixture, a magnesium/aluminum mixture, a magnesium/indium mixture, an aluminum/aluminum oxide (Al$_2$O$_3$) mixture, a lithium/aluminum mixture, or aluminum is suitable. It should be noted that a case where any one of the anode and the cathode of the organic EL element is transparent or translucent in order to transmit emitted light is advantageous because light emission luminance is improved.

Light-Emitting Layer

The light-emitting layer is a layer which emits light after excitons have been generated through the recombination of holes and electrons injected respectively from an anode and a cathode. The light-emitting layer preferably includes an organic light-emitting material and a host material. As the organic light-emitting material, there may be used one kind or two or more kinds selected from the compounds of formula (I). In order that the organic EL element of the present invention exhibits high luminous efficiency, it is important to confine, in the organic light-emitting material, singlet excitons and triplet excitons generated in the organic light-emitting material. Accordingly, it is preferred to use the host material in addition to the organic light-emitting material in the light-emitting layer. As the host material, there may be used an organic compound having a higher value of at least any one of excited singlet energy and excited triplet energy than those of the organic light-emitting material of the present invention. This allows singlet excitons and triplet excitons generated in the organic light-emitting material of the present invention to be confined in the molecule of the organic light-emitting material of the present invention and allows the luminous efficiency to be exhibited sufficiently. In the organic EL element of the present invention, light is emitted from the organic light-emitting material of the present invention included in the light-emitting layer.

In case of using the host material, the content of the organic light-emitting material of the present invention in the light-emitting layer fall within the range of 1 to 50 wt %, preferably 1 to 20 wt %.

The host material in the light-emitting layer is preferably an organic compound which has a hole-transporting ability and/or an electron-transporting ability, prevents an emission wavelength from becoming longer, and has a high glass transition temperature.

The host material may be a polymer, for example poly (N-vinylcarbazole) or polysilane. The host material may, however, be a small molecule, for example 4,4'-N,N'-dicarbazolebiphenyl (CDP=CBP), 2,6-bis(N-carbazolyl)pyridincphenyl (mCP), 3,3-di(9H-carbazol-9-yl)biphenyl (mCBP),

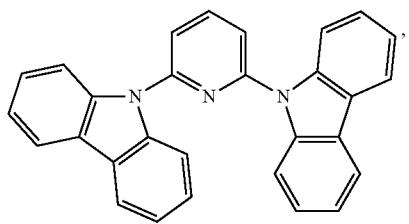

(PYD2)

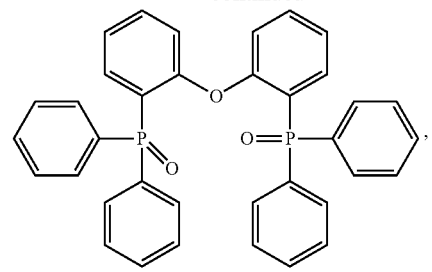

(DPEPO)

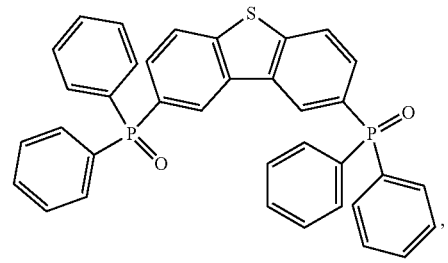

(PPT)

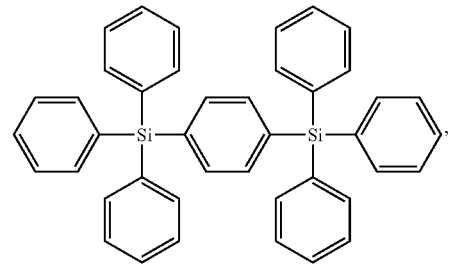

(UGH-2)

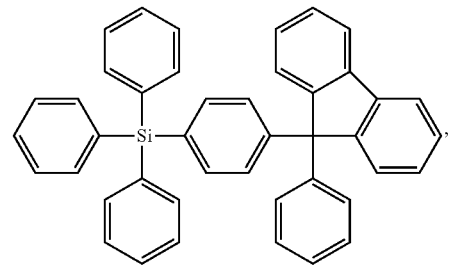

(TPSi-F)

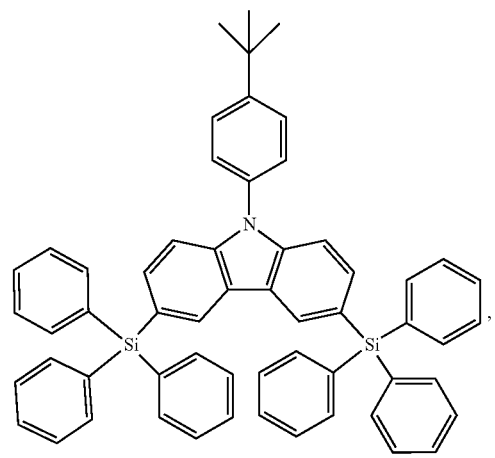

(CzSi)

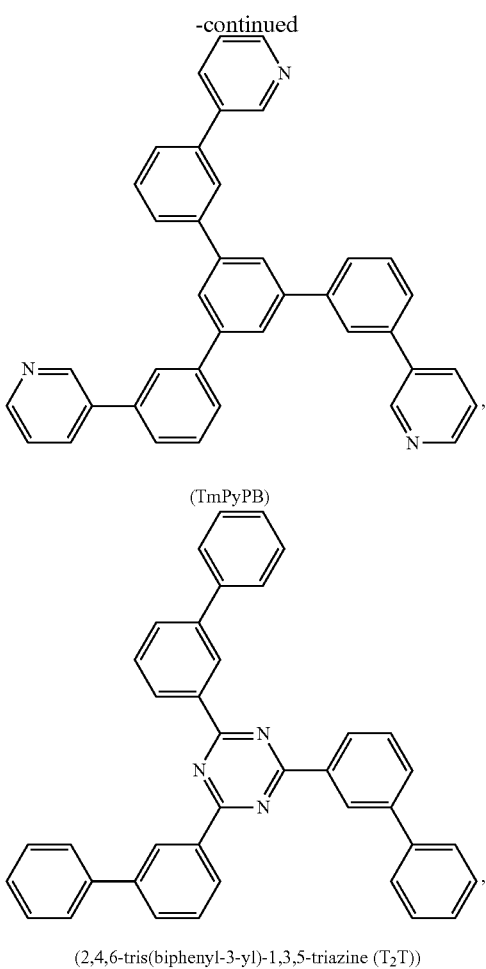

(TmPyPB)

(2,4,6-tris(biphenyl-3-yl)-1,3,5-triazine (T₂T))

or tertiary aromatic amines, for example tris(4-carbazoyl-9-ylphenyl)amine (TCTA).

Injecting Layer

The injecting layer refers to a layer to be provided between an electrode and an organic layer for the purposes of reducing a driving voltage and improving a light emission luminance. The injecting layer includes a hole-injecting layer and an electron-injecting layer, and may be provided between the anode and the light-emitting layer or the hole-transporting layer, and between the cathode and the light-emitting layer or the electron-transporting layer. The injecting layer may be provided as necessary.

Customarily used hole injection materials include α-NPD, CuPc, MTDATA, or dipyrazino[2,3-f:2',3'-h]quinoxaline-2,3,6,7,10,11-hexacarbonitrile (HAT-CN). Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly (3,4-ethylenedioxythiophene)/poly(4-styrenesulfonate) also called PEDOT/PSS.

Lithium-comprising organometallic compounds such as 8-hydroxyquinolatolithium (Liq), CsF, NaF, KF, Cs$_2$CO$_3$ or LiF may be applied between the electron transport layer and the cathode as an electron injection layer in order to reduce the operating voltage.

Blocking Layer

The blocking layer is capable of blocking charges (electrons or holes) and/or excitons present in the light-emitting layer from diffusing to the outside of the light-emitting layer. The electron-blocking layer may be arranged between the light-emitting layer and the hole-transporting layer, and blocks electrons from passing through the light-emitting layer toward the hole-transporting layer. Similarly, the hole-blocking layer may be arranged between the light-emitting layer and the electron-transporting layer, and blocks holes from passing through the light-emitting layer toward the electron-transporting layer. The blocking layer may also be used for blocking excitons from diffusing to the outside of the light-emitting layer. That is, the electron-blocking layer and the hole-blocking layer may each have a function of an exciton-blocking layer as well. The electron-blocking layer or exciton-blocking layer as used herein is meant to include a layer having a function of an electron-blocking layer and an exciton-blocking layer in one layer.

Hole-Blocking Layer

The hole-blocking layer has a function of the electron-transporting layer in a broad sense. The hole-blocking layer has a role in blocking holes from reaching the electron-transporting layer while transporting electrons. This can improve the probability of recombination of electrons and holes in the light-emitting layer. As a material for the hole-blocking layer, a material for the electron-transporting layer to be described below may be used as necessary.

Electron-Blocking Layer

The electron-blocking layer has a function of transporting holes in a broad sense. The electron-blocking layer has a role in blocking electrons from reaching the hole-transporting layer while transporting holes. This can improve the probability of recombination of electrons and holes in the light-emitting layer.

Exciton-Blocking Layer

The exciton-blocking layer refers to a layer for blocking excitons, which are generated by the recombination of holes and electrons in the light-emitting layer, from diffusing to a charge-transporting layer. The insertion of this layer allows excitons to be efficiently confined in the light-emitting layer, which can improve the luminous efficiency of an element. The exciton-blocking layer may be inserted on any of the anode side and the cathode side of the adjacent light-emitting layer, and may be simultaneously inserted on both of the sides. That is, when the exciton-blocking layer is provided on the anode side, the layer may be inserted between the hole-transporting layer and the light-emitting layer so as to be adjacent to the light-emitting layer. When the exciton-blocking layer is inserted on the cathode side, the layer may be inserted between the light-emitting layer and the cathode so as to be adjacent to the light-emitting layer. Further, the hole-injecting layer, the electron-blocking layer, and the like may be provided between the anode and the exciton-blocking layer adjacent to the anode side of the light-emitting layer, and the electron-injecting layer, the electron-transporting layer, the hole-blocking layer, and the like may be provided between the cathode and the exciton-blocking layer adjacent to the cathode side of the light-emitting layer. In the case of providing the blocking layer, it is preferred that at least any one of the excited singlet energy and excited triplet energy of a material to be used as the blocking layer be higher than the excited singlet energy and excited triplet energy of a light-emitting material.

Hole blocker materials typically used are 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato)aluminum(III) (BAlq), phenothiazine S,S-dioxide derivates and 1,3,5-tris(N-phenyl-2-benzylimidazolyl)benzene) (TPBI), TPBI also being suitable as electron-transport material. Further suitable hole blockers and/or electron conductor materials are 2,2',2"-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di(naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris(2,4,6-trimethyl-3-(pyridin-3-yl)phenyl)borane, 2,9-bis(naphthalene-2-yl)-4,7-diphenyl-1,10-phenanthroline, 1-methyl-2-(4-(naphthalene-2-yl)phenyl)-1H-imidazo[4,5-f][1,10]phenanthroline,

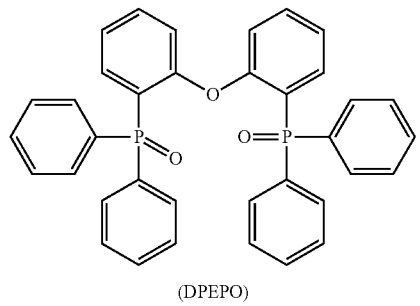 [SMILES: O=P(c1ccccc1)(c1ccccc1)c1ccccc1Oc1ccccc1P(=O)(c1ccccc1)c1ccccc1]

(DPEPO)

and 2,4,6-tris(biphenyl-3-yl)-1,3,5-triazine (T2T).

Hole-Transporting Layer

The hole-transporting layer is formed of a hole-transporting material having a function of transporting holes. The hole-transporting layer may be provided in a single layer or a plurality of layers.

The hole-transporting material has any of hole-injecting or -transporting property and electron-blocking property, and may be an organic material or an inorganic material. An applicable known hole-transporting material is exemplified by a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, or a conducting polymeric oligomer, particularly a thiophene oligomer. However, preferably used are a porphyrin compound, an aromatic tertiary amine compound, and a styrylamine compound, and more preferably used is an aromatic tertiary amine compound. Customarily used hole-transporting molecules are selected from the group consisting of

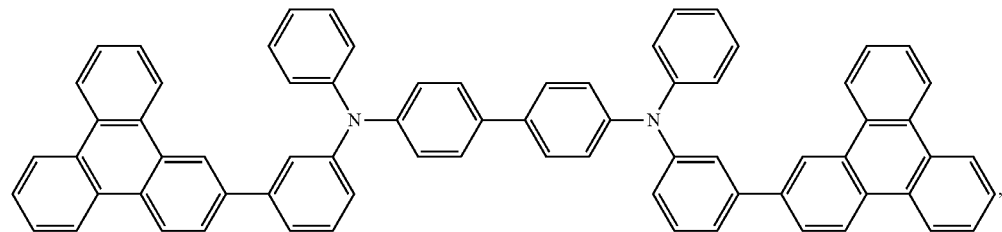

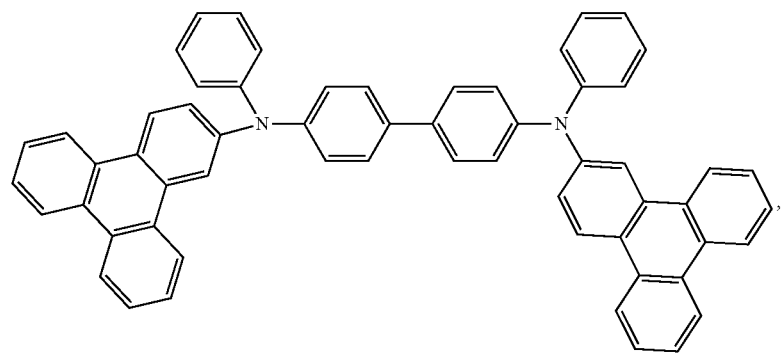

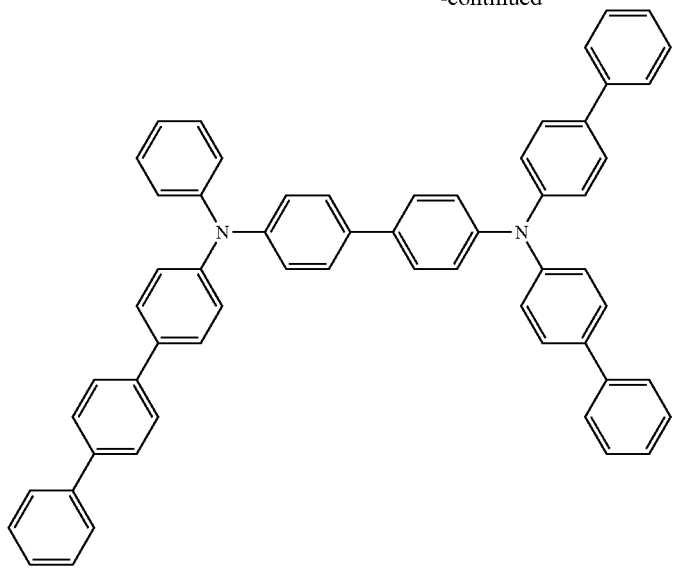
(4-phenyl-N-(4-phenylphenyl)-N-[4-[4-(N-[4-(4-phenyl-phenyl)phenyl]anilino)phenyl]phenyl]aniline),
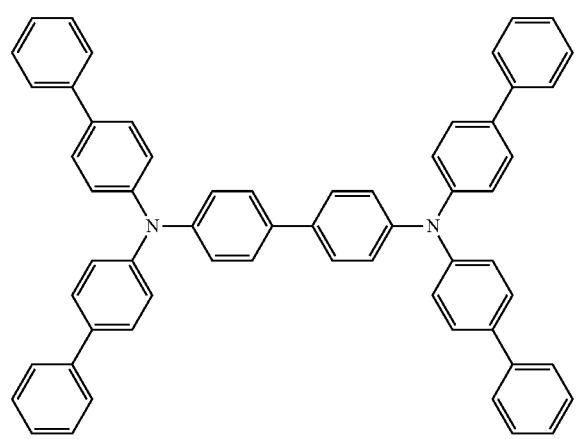 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
(4-phenyl-N-(4-phenylphenyl)-N-[4-[4-(4-phenyl-N-(4-phenylphenyl)anilino)phenyl]phenyl]aniline),
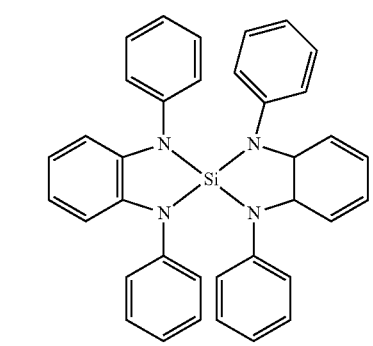 [SMILES: C1=CC2C(C=C1)N(c1ccccc1)[Si]1(N(c3ccccc3)c3ccccc3N1c1ccccc1)N2c1ccccc1]
(4-phenyl-N-[4-(9-phenylcarbazol-3-yl)phenyl]-N-(4-phenylphenyl)aniline)
(1,1',3,3'-tetraphenylspiro[1,3,2-benzodiazasilole-2,2'-3a,7a-dihydro-1,3,2-benzodiazasilole]),

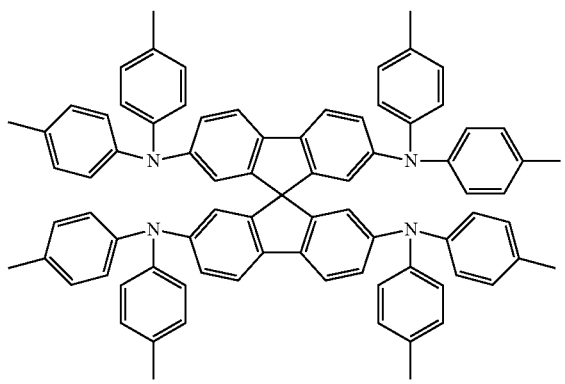

(N2,N2,N2',N2',N7,N7,N7',N7'-octakis(p-tolyl)-9,9'-spirobi[fluorene]-2,2',7,7'-tetramine), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]-cyclohexane (TAPC), N,N'-bis(4-methylphenyl)-N,N'-bis(4-ethylphenyl)-[1,1'-(3,3'-dimethyl)-biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)2-methylphenyl](4-methylphenyl)methane (MPMP), 1-phenyl-3-[p-(diethylamino)styryl]5-[p-(diethylamino)phenyl]pyrazoline (PPR or DEASP), 1,2-trans-bis(9H-carbazol9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolyl)amino9,9-spirobifluorene (spiro-TTB), N,N'-bis(naphthalen-1-yl)-N,N'-bis(phenyl)9,9-spirobifluorene (spiro-NPB) and 9,9-bis(4-(N,N-bis-biphenyl-4-yl-amino)phenyl-9Hfluorene, benzidine compounds such as N,N'-bis(naphthalen-1-yl)-N,N'-bis(phenyl)benzidine and porphyrin compounds such as copper phthalocyanines,

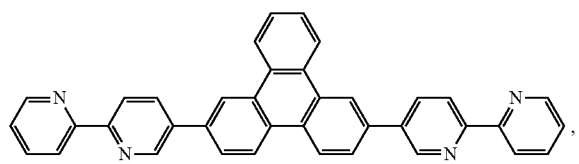

(BPY-TP2)

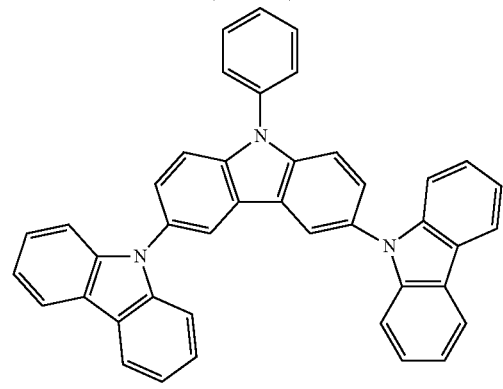

(Tris-PCz)

and CzSi. In addition, polymeric hole-injection materials can be used such as poly(N-vinylcarbazole) (PVK), poly- thiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

Electron-Transporting Layer

The electron-transporting layer is formed of a material having a function of transporting electrons. The electron-transporting layer may be provided in a single layer or a plurality of layers.

An electron-transporting material (may also serve as a hole-blocking material) has only to have a function of transporting electrons, which are injected from the cathode, to the light-emitting layer. An applicable electron-transporting layer is exemplified by a nitro-substituted fluorene derivative, a diphenylquinone derivative, a thiopyran dioxide derivative, car-bodiimide, a fluorenylidenemethane derivative, an anthraquinodimethane derivative, an anthrone derivative, or an oxadiazole derivative. In addition, in oxadiazole derivative, a thiadiazole derivative in which an oxygen atom of an oxadiazole ring is substituted by a sulfur atom, or a quinoxaline derivative having a quinoxaline ring known as an electron-withdrawing group may also be used as the electron-transporting material. In addition, a polymer material obtained by introducing any of those materials into a polymer chain, or a polymer material including any of those materials in a polymer main chain may also be used. Suitable electron-transporting materials comprise 1,3,5-tris(N-phenyl-2-benzylimidazolyl)benzene (TPBi),

(BPY-TP2)

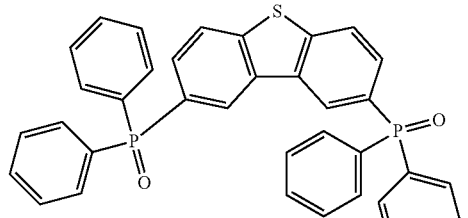

(PPT)

metals chelated with oxinoid compounds, such as tris(8-hydroxyquinolato)aluminum (Alq3), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4phenyl-5-(4-t-butylphenyl)-1,2,4-triazole (TAZ).

Examples of possible element structures are shown below:

ITO (100 nm)/α-NPD (35 nm)/CBP: 6% by weight cpd. of formula (I) (15 nm)/TPBi (65 nm)/LiF (0.8 nm)/Al (80 nm)

ITO (100 nm)/α-NPD (40 nm)/mCP/PPT: 6% by weight cpd. of formula (I) (20 nm)/PPT (40 nm)/LiF (0.8 nm)/Al (80 nm)

ITO (30-100 nm)/α-NPD (60 nm)/mCP: 6% by weight cpd. of formula (I) (20 nm)/Bphen (40 nm)/MgAg (100 nm)/Ag (20 nm)

ITO (30-100 nm)/α-NPD (60 nm)/PYD2: 6% by weight cpd. of formula (I) (20 nm)/Bphen (40 nm)/MgAg (100 nm)/Al (20 nm)

ITO/α-NPD (35 nm)/6% by weight cpd. of formula (I): CBP (15 nm)/TPBi (65 nm)/LiF (0.8 nm)/Al (80 nm)

ITO (100 nm)/HAT-CN (10 nm)/Tris-PCz (30 nm)/CBP: 3, 6, 10, or 15% by weight cpd. of formula (I) (30 nm)/BPY-TP2 (40 nm)/LiF (0.8 nm)/Al (100 nm)

ITO (100 nm)/α-NPD (35 nm)/CBP (10 nm)/DPEPO: 6 to 12% by weight cpd. of formula (I) (15 nm)/DPEPO (10 nm)/TPBi (65 nm)/LiF (0.5 nm)/Al (80 nm)]

ITO (100 nm)/HAT-CN (10 nm)/Tris-PCz (30 nm)/mCBP: 6 to 12% by weight cpd. of formula (I) (30 nm)/T2T (10 nm)/Bpy-TP2 (40 nm)/LiF (0.8 nm)/Al (100 nm)

ITO (100 nm)/α-NPD (30 nm)/TCTA (20 nm)/CzSi (10 nm)/DPEPO: 6 to 12% by weight cpd. of formula (I) (20 nm)/DPEPO (10 nm)/TPBi (30 nm)/LiF (0.8 nm)/Al (100 nm)

ITO: indium/tin oxide; α-NPD: 4,4'-bis[N-(1-naphthyl)-N-phenylamino]biphenyl; CBP: 4,4'-N,N'-dicarbazolebiphenyl; TPBi: 1,3,5-tris(N-phenyl-2-benzylimidazolyl)benzene; mCP: 2,6-bis(N-carbazolyl)pyridine; PPT:

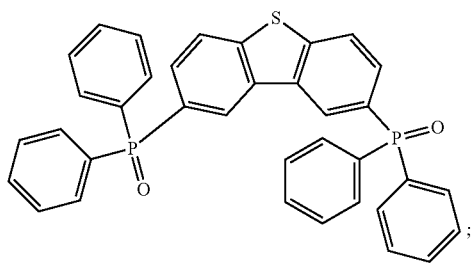 [SMILES: O=P(c1ccccc1)(c1ccccc1)c1ccc2sc3ccc(P(=O)(c4ccccc4)c4ccccc4)cc3c2c1]

Bphen: 4,7-diphenyl-1,10-phenanthroline; PYD2:

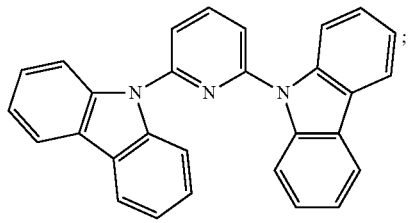 [SMILES: c1cc(-n2c3ccccc3c3ccccc32)nc(-n2c3ccccc3c3ccccc32)c1]

HAT-CN: dipyrazino[2,3-f:2',3'-h]quinoxaline-2,3,6,7,10,11-hexacarbonitrile; Tris-PCz:

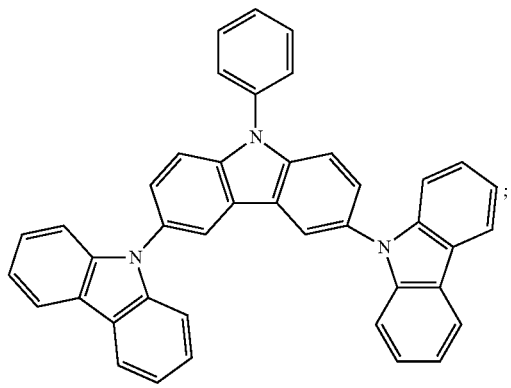 [SMILES: c1ccc(-n2c3ccc(-n4c5ccccc5c5ccccc54)cc3c3cc(-n4c5ccccc5c5ccccc54)ccc32)cc1]

BPY-TP2:

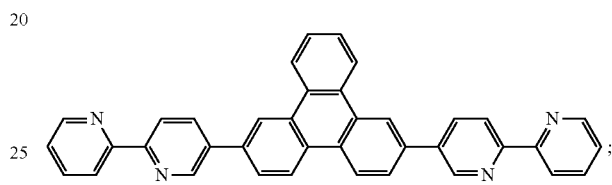

DPE-PO:

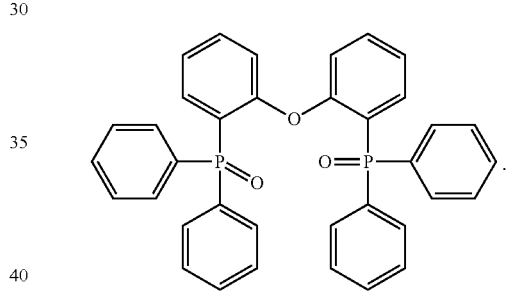

The organic EL element emits light when an electric field is applied between an anode and a cathode of the resultant element.

The organic EL element of the present invention may be applied to any of a single element, an element formed of a structure with arrangement in an array fashion, and a structure in which an anode and a cathode are arranged in an X-Y matrix fashion.

According to the present invention, there is provided an element having significantly improved luminous efficiency as compared to a conventional element using light emission from a singlet state by incorporating the organic light-emitting material having a specific skeleton of the present invention into the light-emitting layer which emits delayed fluorescence. The element can exhibit excellent performance when being applied to a full-color or multi-color panel. The element may also be utilized in a backlight, lighting, and the like.

The above compounds of formula (I) can be used in electrophotographic photoreceptors, photoelectric converters, sensors, dye lasers, solar cell devices and organic light emitting elements.

The compounds of the present invention can be synthesized using copper catalyzed Ullmann conditions or palladium catalyzed Buchwald-Hartwig conditions. Suitable phthalimide and naphthalimide base skeletons are either commercially available, or can be obtained by processes known to those skilled in the art. Reference is made to Organic Letters, 13(20) (2011) 5532-5535, WO2007120788A1, H.-Y. Wang et al., Spectrochimica Acta Part A 93 (2012) 343-347, Georgi H. Dobrikov et al., Cent. Eur. J. Chem. 9(6) (2011) 1126-1132, S. Wang et al., Synthetic Metals 150 (2005) 33-38 and Yi Wang et al., Dyes and Pigments 86 (2010) 190-196.

The following examples are included for illustrative purposes only and do not limit the scope of the claims. Unless otherwise stated, all parts and percentages are by weight.

EXAMPLES

Example 1

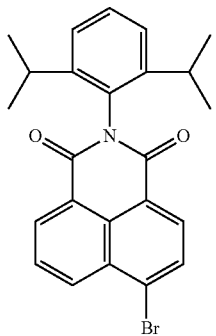
(1a)

a) The compound 1a is prepared from 4-bromo-1,8-naphthalenedicarboxylic acid anhydride and 2,6-diisopropylaniline according to the synthetic procedure described in Organic Letters, 13(20) (2011) 5532-5535.

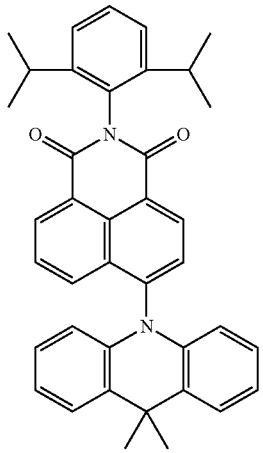
(B-4)

b) The product from example 1a (2.29 mmol), dimethylacridine (2.29 mmol), tris(dibenzylideneacetone) dipalladium (0.046 mmol), tri-tert-buthylphosphine (0.092 mmol), sodium t-buthoxide (3.44 mmol) and 12.5 ml of toluene are placed in a 50 ml flask. The mixture is stirred at 110° C. overnight and cooled. The mixture is washed with $H_2O$ and sat. $NaCl_{aq}$, then the aqueous layer is extracted with ethyl acetate. The combined organic layer is dried over MgSO4 subsequently concentrated under reduced pressure. A orange solid, compound (B-4), is obtained by washing with hexane and drying in vacuum. (Yield: 80.5%). The product is subsequently purified using zone sublimation. $^1$H-NMR (ppm, $CDCl_3$): 8.86 (d, 1H), 8.68 (d, 1H), 8.12 (d, 1H), 7.84 (d, 1H), 7.68 (td, 1H), 7.55 (dd, 2H), 7.49 (d, 1H), 7.36 (d, 2H), 6.97 (td, 2H), 6.90 (td, 2H), 6.04 (dd, 2H), 2.83 (m, 2H), 1.85 (s, 3H), 1.80 (s, 3H), 1.2 (t, 12H).

Example 2

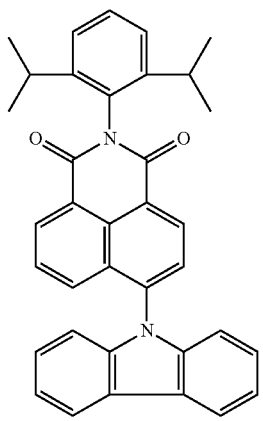
(B-1)

The compound B-1 is prepared according to the method described in Example 1 using carbazole in place of dimethylacridine.

$^1$H-NMR (ppm, $CDCl_3$): 8.86 (d, 1H), 8.73 (d, 1H), 8.24 (d, 2H), 7.97 (d, 1H), 7.88 (d, 1H), 7.68 (t, 1H), 7.51 (t, 1H), 7.38 (m, 6H), 7.11 (d, 2H), 2.83 (m, 2H), 1.21 (t, 12H).

Example 3

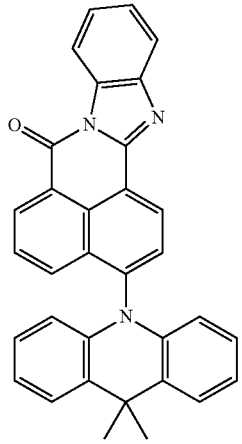
(B-13)

The compound B-13 is prepared according to the method described in Example 1 using 3-bromo-7H-benzimidazo[2,1-a]benz[de]isoquinoline-7-one in place of the compound 1a.

$^1$H-NMR (ppm, CDCl$_3$): 9.08 (d, 1H), 8.86 (d, 1H), 8.61 (m, 1H), 8.14 (d, 1H), 7.94 (m, 1H), 7.86 (d, 1H), 7.72 (t, 1H), 7.54 (m, 4H), 6.96 (t, 2H), 6.88 (t, 2H), 6.03 (d, 2H), 1.87 (s, 3H), 1.78 (s, 3H).

Application Example 1 a) Photoluminescent Characterization in Neat Film

On a silicon substrate, compound

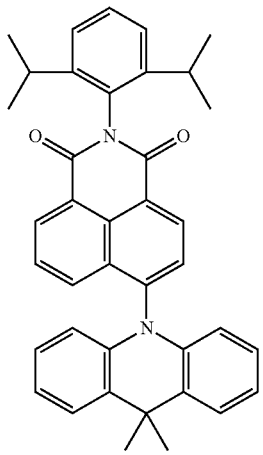

(B-4)

is vacuum-deposited in a thickness of 50 nm. Absorption, fluorescent spectra (excitation at 354 nm) and photoelectron yield spectroscopy of the film are measured, subsequently HOMO and LUMO (eV) of the compound are estimated as 6.14 eV and 3.90 eV, respectively.

b) Photoluminescent Characterization in Host-Guest Film

On a silicon substrate, mCBP doped with 9.8 w % of compound (B-4) is co-deposited in a thickness of 60 nm. The time-resolved and temperature-dependent emission spectra of the host-guest film are measured by photoluminescence spectroscopy with a streak camera. The prompt (0-15 ns) and delayed (0.1-2 ms) fluorescent components and the temperature dependency are observed as shown Table 1. The host-guest film shows an emission peak at 601 nm in PL spectrum.

TABLE 1

Temperature dependence of PL emission of co-deposited film (mCBP doped with 9.8 w % of compound (B-4)) (streak camera)

| Temperature (K.) | Prompt PL intensity (a.u.) | Delayed PL intensity (a.u.) |
| --- | --- | --- |
| 8 | 0.875 | 0.060 |
| 68 | 0.833 | 0.256 |
| 139 | 0.875 | 0.720 |
| 199 | 0.938 | 0.970 |
| 249 | 0.917 | 1 |
| 279 | 1 | 0.976 |
| 298 | 0.958 | 0.958 |

These results indicate that compound (B-4) is a TADF material.

Application Example 2

An organic light emitting device (OLED) is fabricated by vacuum deposition of ITO (100 nm)/dipyrazino[2,3-f:2',3'-h]quinoxaline-2,3,6,7,10,11-hexacarbonitrile (HAT-CN) (10 nm)/

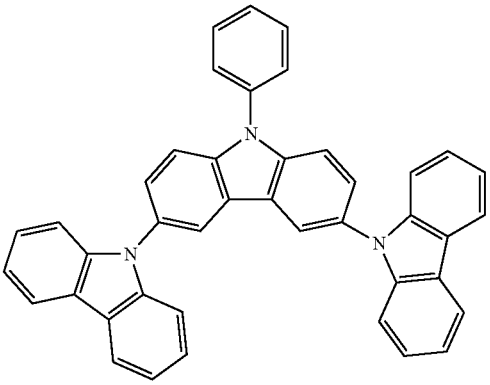 [SMILES: c1ccc(-n2c3ccc(-n4c5ccccc5c5ccccc54)cc3c3cc(-n4c5ccccc5c5ccccc54)ccc32)cc1]

(Tris-PCz, 30 nm)/89.3 w % 3,3-di(9H-carbazol-9-yl)biphenyl (mCBP):10.7 w % compound B-4 (30 nm)/2,4,6-tris(biphenyl-3-yl)-1,3,5-triazine (T2T, 10 nm)/

(Bpy-TP2, 40 nm)/LiF (0.8 nm)/Al (100 nm) on a glass substrate, subsequently the device is encapsulated and the performance of the device is evaluated. The device shows an emission peak at 616 nm in elec-troluminescence (EL) spectrum with an external quantum efficiency (EQE) of 7.5%.

The invention claimed is:

1. A compound of formula

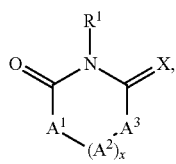

(I)

wherein

X is O, or NR$^2$;

R$^1$ is a C$_1$-C$_{25}$alkyl group, a C$_6$-C$_{10}$aryl group which is optionally substituted by one or more groups R$^8$;

R$^2$ is a C$_1$-C$_6$alkyl group, a C$_2$-C$_4$alkenyl group, or a C$_6$-C$_{10}$aryl group, which is optionally substituted by one or more groups R$^8$; or R$^1$ and R$^2$ together form a ring

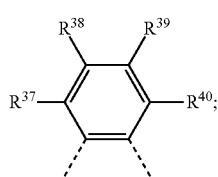

wherein
R$^{37}$, R$^{38}$, R$^{39}$ and R$^{40}$ are independently of each other H, D, F, Cl, a C$_1$-C$_{25}$alkyl group, a C$_1$-C$_{25}$alkoxy group, a C$_6$-C$_{10}$aryl group which may optionally be substituted by one or more groups R$^8$,
A$^1$, A$^2$ and A$^3$ are C,
x is 0, or 1,
if x is 0,
A$^1$ and A$^3$ are connected via a double bond and together form a ring $$\underset{R^4\ \ R^5}{R^3-\!\!=\!\!-R^6},$$

if x is 1, then X is NR$^2$,
A$^1$ and A$^2$ and A$^2$ and A$^3$ are connected via a single bond and together form a ring system R$^3$, R$^4$, R$^5$, R$^6$, R$^{31}$, R$^{32}$, R$^{33}$, R$^{34}$, R$^{35}$ and R$^{36}$ are independently of each other H, D, F, Cl, a C$_1$-C$_{25}$alkyl group, a C$_1$-C$_{25}$alkoxy group, a C$_6$-C$_{10}$aryl group which may optionally be substituted by one or more groups R$^8$, or a donor group of formula (Xa)

(Xd)

R$^8$ is D, F, Cl, a C$_1$-C$_{12}$alkyl group, a C$_1$-C$_{12}$alkoxy group, or a C$_6$-C$_{10}$aryl group;
X$^1$ is a direct bond, O, S, N(R$^{15}$), C(=O), C(R$^{16}$)(R$^{17}$), B(R$^{18}$), or Si(R$^{19}$)(R$^{20}$),
R$^{10}$, R$^{11}$, R$^{21}$ and R$^{21'}$ are independently of each other H, D, F, Cl, Br, or a C$_1$-C$_{25}$alkyl group;
R$^{15}$, R$^{16}$, R$^{17}$, R$^{18}$, R$^{19}$ and R$^{20}$ are independently of each other H, D, a C$_1$-C$_{25}$alkyl group, or a C$_6$-C$_{14}$aryl group, which can optionally be substituted by one, or more groups selected from a C$_1$-C$_{25}$alkyl group, a C$_1$-C$_{25}$alkoxy group and a C$_6$-C$_{10}$aryloxy group;

with the proviso that at least one of the groups R$^3$, R$^4$, R$^5$, R$^6$, R$^{31}$, R$^{32}$, R$^{33}$, R$^{34}$, R$^{35}$ and R$^{36}$ is a donor group of formula (Xa), or (Xd).

2. The compound according to claim 1, which is a compound of formula (II)

wherein X, R$^1$, R$^3$, R$^4$, R$^5$ and R$^6$ are as defined in claim 1.

3. The compound according to claim 2, which is a compound of formula (IIa)

wherein R$^1$, R$^3$, R$^4$, R$^5$ and R$^6$ are as defined in claim 1.

4. The compound according to claim 1, wherein
R$^3$, R$^4$, R$^5$ and R$^6$ are independently of each other a donor group of formula (Xa), or (Xd) as defined in claim 1; or
R$^3$ and R$^6$ are H and R$^4$ and R$^5$ are independently of each other a donor group of formula (Xa), or (Xd) as defined in claim 1; or
R$^4$ and R$^5$ are H and R$^3$ and R$^6$ are independently of each other a donor group of formula (Xa), or (Xd) as defined in claim 1; or
R$^4$ and R$^6$ are H and R$^3$ and R$^5$ are independently of each other a donor group of formula (Xa), or (Xd) as defined in claim 1; or
R$^3$, R$^4$ and R$^6$ are H and R$^5$ is a donor group of formula (Xa), or (Xd) as defined in claim 1; or
R$^3$, R$^4$ and R$^5$ are H and R$^6$ is a donor group of formula (Xa), or (Xd) as defined in claim 1.

5. The compound according to claim 2, which is a compound of formula

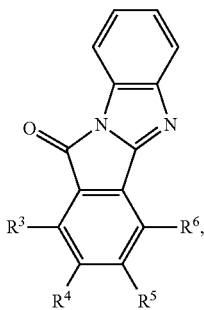

(IIb)

wherein $R^3$, $R^4$, $R^5$ and $R^6$ are as defined in claim 1.

6. The compound according to claim 5, wherein $R^3$, $R^4$, $R^5$ and $R^6$ are independently of each other a donor group of formula (Xa), or (Xd) as defined in claim 1; or $R^3$ and $R^6$ are H and $R^4$ and $R^5$ are independently of each other a donor group of formula (Xa), or (Xd) as defined in claim 1; or $R^4$ and $R^5$ are H and $R^3$ and $R^6$ are independently of each other a donor group of formula (Xa), or (Xd) as defined in claim 1; or $R^3$, $R^4$ and $R^5$ are H and $R^6$ is a donor group of formula (Xa), or (Xd) as defined in claim 1; or $R^3$, $R^4$ and $R^6$ are H and $R^5$ is a donor group of formula (Xa), or (Xd) as defined in claim 1; or $R^3$, $R^5$ and $R^6$ are H and $R^4$ is a donor group of formula (Xa), or (Xd) as defined in claim 1; or $R^4$, $R^5$ and $R^6$ are H and $R^3$ is a donor group of formula (Xa), or (Xd) as defined in claim 1.

7. The compound according to claim 1, which is a compound of formula

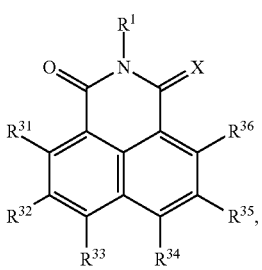

(III)

wherein X, $R^1$, $R^{31}$, $R^{32}$, $R^{33}$, $R^{34}$, $R^{35}$ and $R^{36}$ are as defined in claim 1.

8. The compound according to claim 7, which is a compound of formula

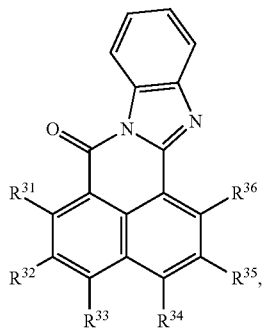

(IIIb)

wherein $R^{31}$, $R^{32}$, $R^{33}$, $R^{34}$, $R^{35}$ and $R^{36}$ are as defined in claim 1.

9. The compound according to claim 8, wherein $R^{31}$, $R^{32}$, $R^{33}$, $R^{35}$ and $R^{36}$ are H and $R^{34}$ is a donor group of formula (Xa), or (Xd) as defined in claim 1; or $R^{31}$, $R^{32}$, $R^{34}$, $R^{35}$ and $R^{36}$ are H and $R^{33}$ is a donor group of formula (Xa), or (Xd) as defined in claim 1; or $R^{31}$, $R^{32}$, $R^{35}$ and $R^{36}$ are H and $R^{33}$ and $R^{34}$ are independently of each other a donor group of formula (Xa), or (Xd) as defined in claim 1.

10. The compound according to claim 1, wherein $R^1$ is a $C_1$-$C_{25}$alkyl group, a group of formula

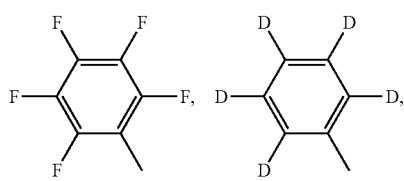

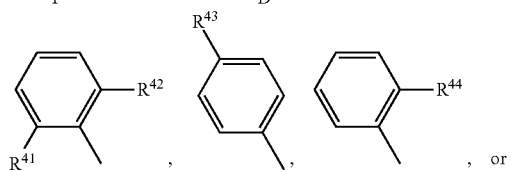

wherein $R^{41}$ and $R^{42}$ are a $C_1$-$C_8$alkyl group;

$R^{43}$ is a $C_1$-$C_8$alkyl group, or a $C_1$-$C_8$alkoxy group;

$R^{44}$ is a $C_1$-$C_8$alkyl group, or a phenyl group; and $R^{45}$ is a $C_1$-$C_8$alkyl group.

11. The compound according claim 1, wherein the donor group is a donor group of formula (Xa), wherein $X^1$ is a direct bond, O, S, C(CH$_3$)(CH$_3$), C(=O), or

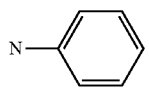

and $R^{10}$ and $R^{11}$ are as defined in claim 1; or a donor group of formula (Xd), wherein $R^{21}$ and $R^{21'}$ are H.

12. The compound according to claim 1, wherein the donor group is a group of formula

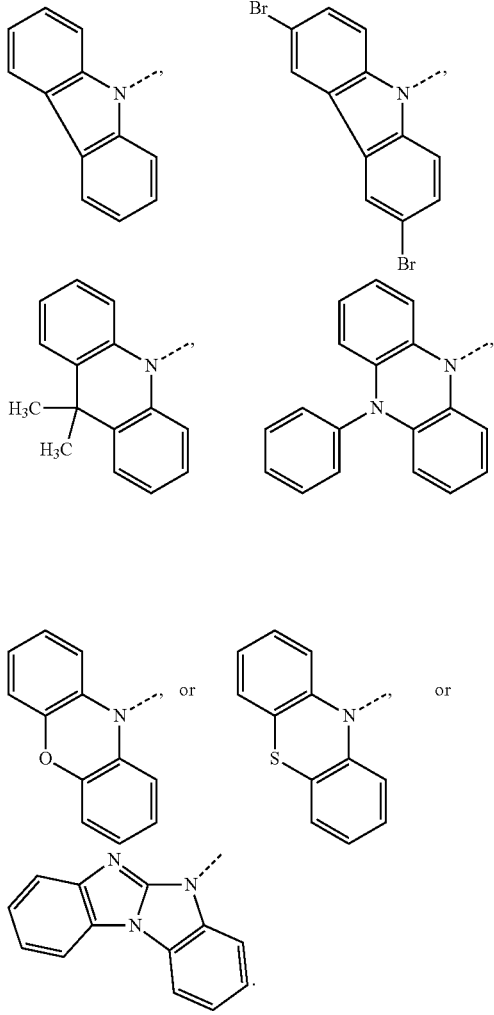

13. A light-emitting layer comprising the compound according claim 1.

14. An organic light emitting element, comprising the compound according to claim 1.

15. The organic light-emitting element according to claim 14, comprising a light-emitting layer comprising a compound according to claim 1 as guest and a host material.

16. The organic light-emitting element according to claim 14, comprising a light-emitting layer comprising a compound according to claim 1 as host and a guest material.

17. The organic light-emitting element according to claim 14, characterized in that it emits delayed fluorescence.

18. A device selected from the group consisting of a electrophotographic photoreceptor, photoelectric converter, sensor, dye laser, solar cell device and organic light emitting element, wherein the device comprises a compound according to claim 1.

19. The compound according to claim 1, wherein the compound is capable of generating delayed fluorescence emission.

20. A compound of formula

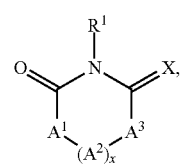

(I)

wherein
X is O, or $NR^2$;
$R^1$ is a $C_1$-$C_{25}$alkyl group, a group of formula

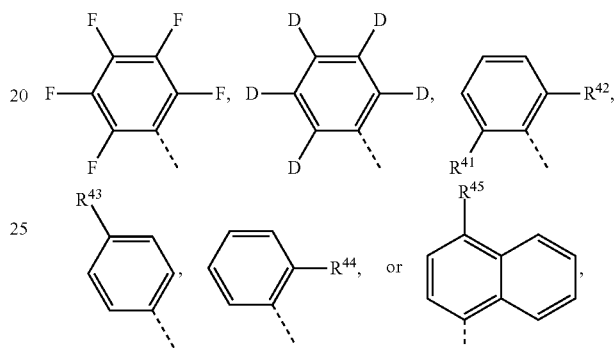

$R^2$ is a $C_1$-$C_6$alkyl group, a $C_2$-$C_4$alkenyl group, or a $C_6$-$C_{10}$aryl group, which is optionally substituted by one or more groups $R^8$; or
$R^1$ and $R^2$ together form a ring

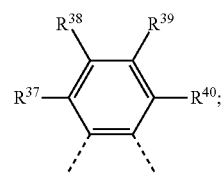

wherein
$R^{37}$, $R^{38}$, $R^{39}$ and $R^{40}$ are independently of each other H, D, F, Cl, a $C_1$-$C_{25}$alkyl group, a $C_1$-$C_{25}$alkoxy group, a $C_6$-$C_{10}$aryl group which may optionally be substituted by one or more groups $R^8$,
$A^1$, $A^2$ and $A^3$ are C,
x is 0, or 1,
if x is 0,
$A^1$ and $A^3$ are connected via a double bond and together form a ring

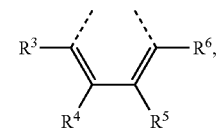

if x is 1,
$A^1$ and $A^2$ and $A^2$ and $A^3$ are connected via a single bond and together form a ring system

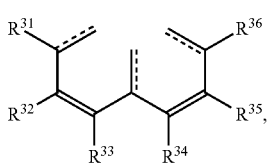

$R^3$, $R^4$, $R^5$, $R^6$, $R^{31}$, $R^{32}$, $R^{33}$, $R^{34}$, $R^{35}$ and $R^{36}$ are independently of each other H, D, F, Cl, a $C_1$-$C_{25}$alkyl group, a $C_1$-$C_{25}$alkoxy group, a $C_6$-$C_{10}$aryl group which may optionally be substituted by one or more groups $R^8$, or a donor group of formula

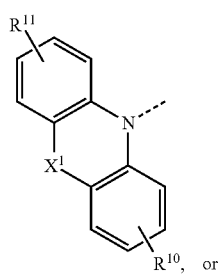

(Xa)

or

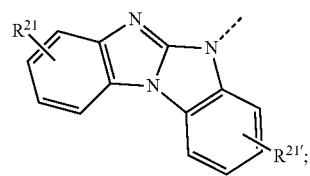

(Xd)

$R^8$ is D, F, Cl, a $C_1$-$C_{12}$alkyl group, a $C_1$-$C_{12}$alkoxy group, or a $C_6$-$C_{10}$aryl group;

$X^1$ is a direct bond, O, S, N($R^{15}$), C(=O), C($R^{16}$)($R^{17}$), B($R^{18}$), or Si($R^{19}$)($R^{20}$), $R^{10}$, $R^{11}$, $R^{21}$ and $R^{21'}$ are independently of each other H, D, F, Cl, Br, or a $C_1$-$C_{25}$alkyl group;

$R^{15}$, $R^{16}$, $R^{17}$, $R^{18}$, $R^{19}$ and $R^{20}$ are independently of each other H, D, a $C_1$-$C_{25}$alkyl group, or a $C_6$-$C_{14}$aryl group, which can optionally be substituted by one, or more groups selected from a $C_1$-$C_{25}$alkyl group, a $C_1$-$C_{25}$alkoxy group and a $C_6$-$C_{10}$aryloxy group;

$R^{41}$ and $R^{42}$ are a $C_1$-$C_8$alkyl group;

$R^{43}$ is a $C_1$-$C_8$alkoxy group;

$R^{44}$ is a $C_1$-$C_8$alkyl group, or a phenyl group;

$R^{45}$ is a $C_1$-$C_8$alkyl group; and wherein at least one of the groups $R^3$, $R^4$, $R^5$, $R^6$, $R^{31}$, $R^{32}$, $R^{33}$, $R^{34}$, $R^{35}$ and $R^{36}$ is a donor group of formula (Xa), or (Xd).

21. A device selected from the group consisting of a electrophotographic photoreceptor, photoelectric converter, sensor, dye laser, solar cell device and organic light emitting element, wherein the device comprises a compound according to claim 20.

* * * * *